(12) United States Patent
Dempsey

(10) Patent No.: US 8,812,077 B2
(45) Date of Patent: Aug. 19, 2014

(54) SYSTEM AND METHOD FOR IMAGE GUIDANCE DURING MEDICAL PROCEDURES

(75) Inventor: James F. Dempsey, Chagrin Falls, OH (US)

(73) Assignee: ViewRay Incorporated, Oakwood Village, OH (US)

( * ) Notice: Subject to any disclaimer, the term of this patent is extended or adjusted under 35 U.S.C. 154(b) by 48 days.

(21) Appl. No.: 13/333,726

(22) Filed: Dec. 21, 2011

(65) Prior Publication Data

US 2012/0165652 A1 Jun. 28, 2012

Related U.S. Application Data

(60) Provisional application No. 61/425,891, filed on Dec. 22, 2010.

(51) Int. Cl.
*A61B 5/055* (2006.01)

(52) U.S. Cl.
USPC .......................................... 600/411; 600/410

(58) Field of Classification Search
USPC .................. 600/411, 414, 439, 443; 335/216
See application file for complete search history.

(56) References Cited

U.S. PATENT DOCUMENTS

| | | | |
|---|---|---|---|
| 5,365,927 | A | 11/1994 | Roemer et al. |
| 5,377,678 | A | 1/1995 | Dumoulin et al. |
| 5,378,989 | A | 1/1995 | Barber et al. |
| 5,722,411 | A | 3/1998 | Suzuki et al. |
| 2003/0011451 | A1 | 1/2003 | Katznelson et al. |
| 2004/0106869 | A1 | 6/2004 | Tepper |
| 2008/0123927 | A1 | 5/2008 | Miga et al. |
| 2009/0171184 | A1 | 7/2009 | Jenkins et al. |
| 2010/0056900 | A1 | 3/2010 | Whitcomb et al. |
| 2010/0113911 | A1 | 5/2010 | Dempsey |
| 2010/0312095 | A1 | 12/2010 | Jenkins et al. |
| 2012/0070056 | A1 | 3/2012 | Krueger et al. |

FOREIGN PATENT DOCUMENTS

EP    2424430 B1    1/2013

OTHER PUBLICATIONS

International Search Report and Written Opinion dated Apr. 13, 2012, for corresponding international application No. PCT/US2011/066605.
Medtronic, Inc., "Image-Guided Surgery Overview", 2010.
Alexandru Patriciu, et al., "Automatic Brachytherapy Seed Placement Under MRI Guidance", IEEE Transactions on Biomedical Engineering , vol. 54, No. 8, Aug. 2007, pp. 1-8.
Dan Stoianovici, et al. "'MRI Stealth' Robot for Prostate Interventions", Minimally Invasive Therapy, 2007, pp. 241-248.

(Continued)

*Primary Examiner* — Michael Rozanski
(74) *Attorney, Agent, or Firm* — Mintz Levin Cohn Ferris Glovsky and Popeo, P.C.

(57) ABSTRACT

A surgical guidance system is disclosed that allows for real-time imaging and patient monitoring during a surgical procedure. The system can include an MRI system for generating real-time images of the patient while surgery is being performed. Prior to surgery, a surgical plan can be created using a planning interface. A control unit receives the real-time image data and the surgical plan, and monitors the image data based on parameters included in the surgical plan. The control-unit monitoring occurs in real-time while the surgical procedure is being performed. The control unit can detect deviations from the surgical plan and/or high-risk patient conditions and instruct an alert unit to issue an alert based on the detected conditions.

29 Claims, 15 Drawing Sheets

(56) References Cited

OTHER PUBLICATIONS

Michael Muntener, MD et al. "Transperineal Prostate Intervention: Robot for fully Automated MR Imaging-System Description and Proof of Principle in a Canine Model". Radiology, vol. 247, No. 2, May 2008, pp. 543-549.

Katarzyna J. Macura, MD, PhD. "Advancements in Magnetic Resonance-Guided Robotic Interventions in the Prostate", Top Magn Reson Imaging, vol. 19, No. 6, Dec. 2008, pp. 297-304.

Pierre C. Mozer, MD, PhD. "Robotic Image-Guided Needle Interventions of the Prostate", Reviews in Urology, vol. 11, No. 1, 2009 pp. 7-15.

Extended European Search Report in European Patent Application No. EP11850577, dated Jul. 9, 2014.

Tokuda, J. et al. "Real-Time Organ Motion Tracking and Fast Image Registration System for MRI-Guided Surgery." *Systems and Computers in Japan Scripta Technica USA*. vol. 37, No. 1. Jan. 2006: 83-92. *Database Inspec* [Online]. The Institution of Electrical Engineers, Stevenage, GB; Jan. 2006.

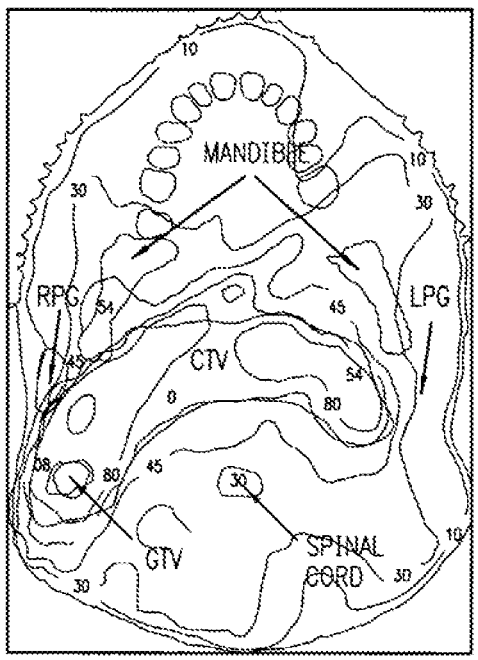
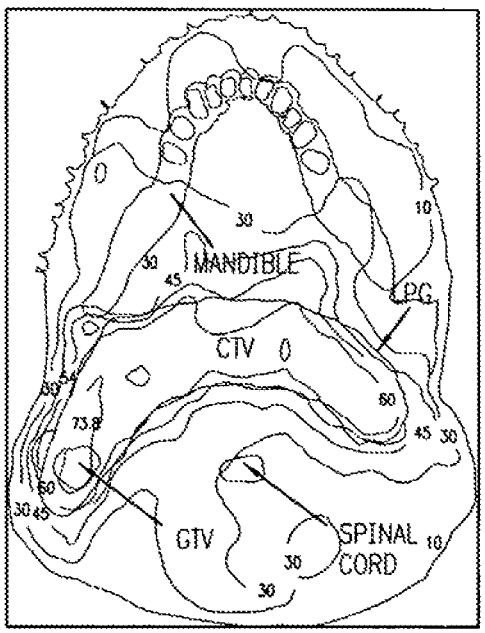
FIGURE 8

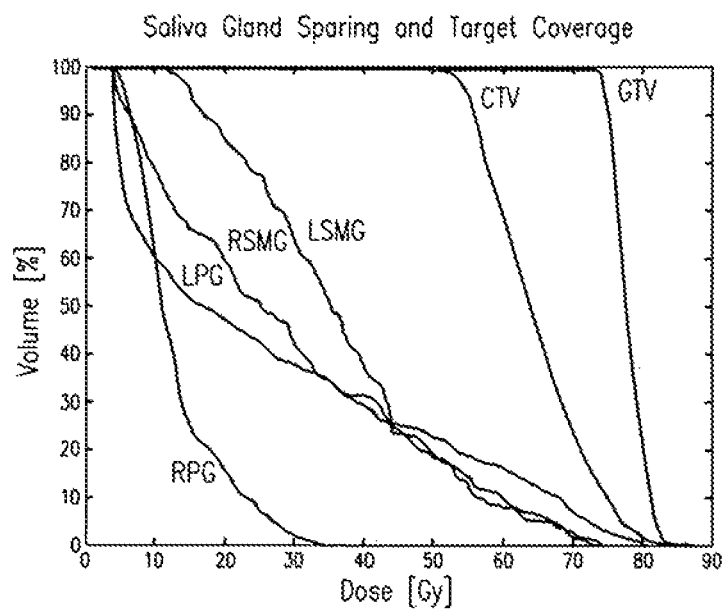
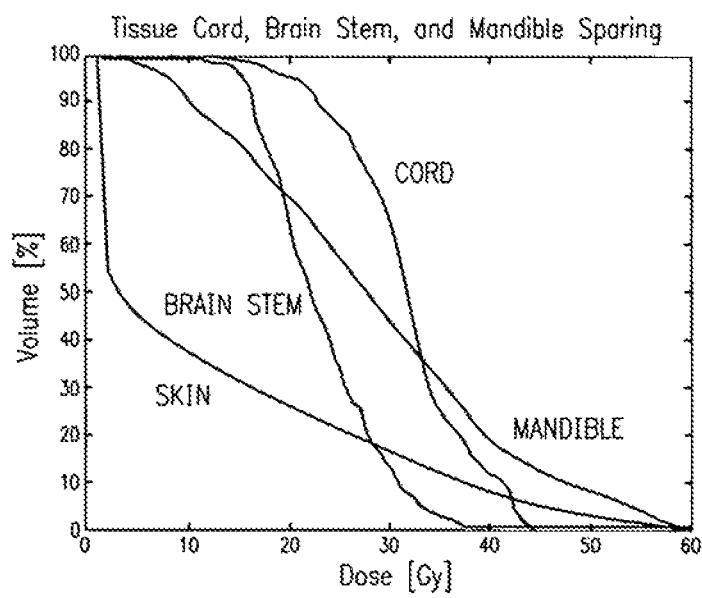
FIGURE 9

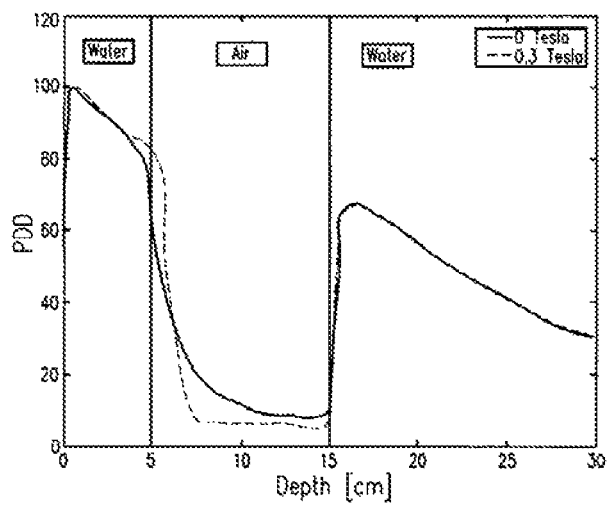
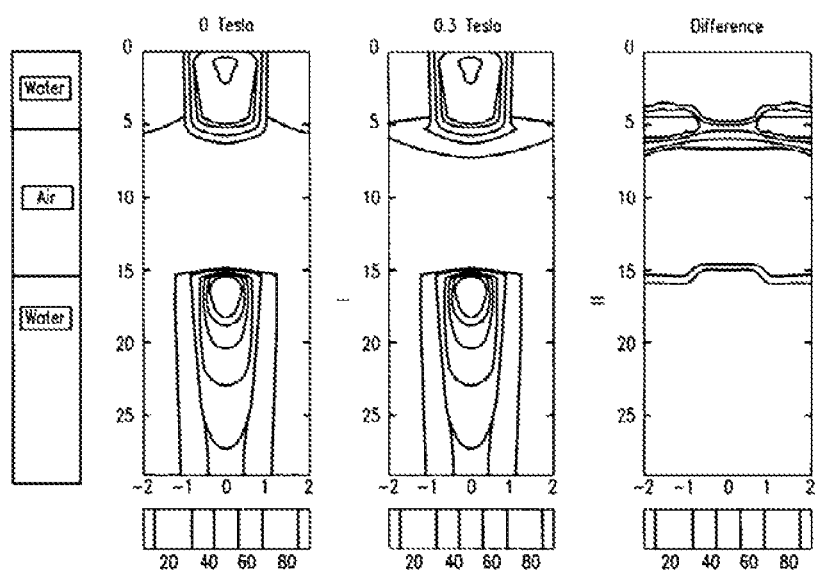
FIGURE 12

SYSTEM AND METHOD FOR IMAGE GUIDANCE DURING MEDICAL PROCEDURES

CROSS-REFERENCE TO RELATED APPLICATIONS

This application claims the benefit of U.S. Provisional Application No. 61/425,891, filed Dec. 22, 2010, which is hereby incorporated herein by reference.

BACKGROUND

1. Technical Field

The present disclosure relates to medical systems and methods, and more particularly to systems and methods for imaging the anatomy of a patient during medical treatment, particularly where the resulting images can be used for enhancing the medical treatment.

2. Related Art

Many types of medical treatments involve a pre-treatment planning phase. Examples of medical treatments may include such things as medications, physical therapy, radiation treatment, and/or surgical procedures. Pre-treatment planning may include medical imaging of patient anatomy, such as x-ray, computed tomography (CT), and/or magnetic resonance imaging (MRI). The images can then be used to assist a physician with deciding on a course of treatment, and preparing a detailed plan for carrying out the medical treatment.

For example, where a medical treatment involves a surgical procedure, a surgical plan is commonly prepared prior to performing the actual surgery. In some cases, a patient undergoes some form of preoperative medical imaging so that the surgical team can review images of the patient's anatomy as part of the surgical planning process. Also, in some cases the preoperative images can be used during the surgical procedure. Image-guided surgery (IGS) is a general term used for a surgical procedure where the surgeon can employ tracked surgical instruments in conjunction with preoperative or intraoperative planar images in order to indirectly guide the procedure. Most image-guided surgical procedures are minimally invasive.

Surgery can include, but is not limited to, any one or more of the following procedures:

Incision—puncturing or cutting into an organ, tumor, or other tissue.

Excision—cutting out an organ, tumor, or other tissue.

Resection—partial removal of an organ or other bodily structure.

Reconnection of organs, tissues, etc., particularly if severed. Resection of organs, such as intestines, typically involves reconnection. Internal suturing or stapling may be used for the reconnection. Surgical connection between blood vessels or other tubular or hollow structures, such as loops of intestine, is called anastomosis.

Ligation—tying off blood vessels, ducts, or "tubes."

Grafting—severing pieces of tissue cut from the same (or different) body, or flaps of tissue still partially connected to the body, but resewn for rearranging or restructuring of an area of the body in question. Although grafting is often used in cosmetic surgery, it is also used in other surgery. Grafts may be taken from one area of the patient's body and inserted to another area of the body. An example is bypass surgery, where clogged blood vessels are bypassed with a graft from another part of the body. Alternatively, grafts may be from other persons, cadavers, or animals.

Insertion of prosthetic parts. Examples of prosthetic parts can include pins or screws for setting and holding together bones; prosthetic rods or other prosthetic parts for replacing sections of bone; plates that are inserted to replace a damaged area of a skull; so-called artificial parts, for example artificial hips, used to replace damaged anatomy; heart pacemakers or valves; or many other types of known prostheses.

Creation of a stoma, which is a permanent or semi-permanent opening in the body.

Organ or tissue transplantation, where a donor organ (taken out of a donor's body) is inserted into a recipient's body and connected to the recipient in all necessary ways (blood vessels, ducts, etc.).

Arthrodesis—surgical connection of adjacent bones so the bones can grow together into one. Spinal fusion is an example of arthrodesis, where adjacent vertebrae are connected allowing them to grow together into one piece.

Modification of tissues, e.g., the digestive tract in bariatric surgery for weight loss.

Repair of a fistula, hernia, stoma, or prolapse.

Ablation or destruction of tissues through the use of heat, cold, electrical current, radiation, or other cell-trauma inducing technology.

Angioplasty, endoscopy, or implantation of devices.

Clearing clogged ducts, blood or other vessels.

Removal of calculi (stones).

Draining of accumulated fluids.

Debridement, which involves the removal of dead, damaged, or diseased tissue.

Exploration to aid or confirm a diagnosis.

Sampling of tissue to aid or confirm a diagnosis.

Amputation, replantation, or reconstruction of tissues or organs.

Some conventional IGS systems include a planar imaging system and a hand-held surgical probe. The planar imaging system is used to take a preoperative or intraoperative "snap shot" of the patient's anatomy in order to locate the patient's anatomy and plan the surgical procedure. During the surgical procedure, some IGS systems include the ability to track the surgical probe position relative to the planar, static image. In such cases, the IGS system includes a display for displaying the static image beneath an image representative of the surgical probe. In some IGS systems, the probe location can be displayed over patient anatomy, where patient anatomy is displayed as three orthogonal, planar image slices on a workstation-based 3D imaging system.

An example of an IGS system is StealthStation®, which is a product offered by Medtronic, Inc. The Medtronic StealthStation® IGS system utilizes electromagnetic and optical tracking technology to determine the location of surgical instruments within a patient during a surgical procedure. The system uses previously-prepared coregistered sectional 2-D images, which are combined using known algorithms to produce 3-D images. The system can then superimpose the position of the instrument over the images so that the surgeon can observe the location of the instrument during a surgical procedure. Such IGS systems may use any of a variety of different tracking techniques, including mechanical, optical, ultrasonic, and electromagnetic technologies to track the probe relative to the static images. Such systems have followed a paradigm where the patient's anatomy is assumed to be static and unmoving during a surgical procedure, and the focus has been attempting to track the "proper" location of the surgical probe or instrument. Such systems also assume that the surgeon will be observing the images, rather than the patient, while positioning the instrument.

As mentioned above, references to treatments can also include medical treatments other than those involving surgical procedures. Another example of a medical treatment is radiation therapy. For example, disease caused by proliferative tissue disorders such as cancer and coronary artery restenosis are sometimes treated with radiation, where the portions of the patient known to contain or suspected to contain disease are irradiated. For this purpose, a radiotherapy planning system is used to first acquire planning images of the diseased portion(s) and surrounding regions.

Radiotherapy planning systems generally include a CT or MRI simulator. CT or MRI radiography is carried out, typically on a single day, before the beginning of therapy to acquire a plurality of coregistered sectional 2-D images. These sectional images are combined using known algorithms to produce 3-D images. These 3-D simulation images are displayed and then analyzed to identify the location of regions of suspected disease to be treated, such as a radiographically evident tumor or regions suspected of microscopic disease spread. These regions to be treated are called radiotherapy targets.

In order to attempt to account for organ motions, the concept of margins and planning target volumes (PTVs) was developed to attempt to irradiate a volume that would hopefully contain the target during most of the irradiation. PTVs include a geometric margin to account for variations in patient geometry or motion. Likewise, the 3-D simulation images are displayed and then analyzed to identify important normal anatomy and tissues that may be damaged by the radiation, such as the spinal cord and lung, to evaluate the potential impact of radiation on the function of these tissues. These regions to be spared or protected from excessive radiation are called critical structures or organs at risk and may also include a margin to account for variations in patient geometry or motion. The delivery of radiation therapy is then traditionally planned on a single static model of radiotherapy targets and critical structures derived from a single set of CT and/or MRI images.

Because the known art does not allow for simultaneous volumetric imaging and therapy, the patient and all of their internal organs need to be repositioned exactly for accurate IGS or radiation dose delivery. However, it is known in the art that exactly repositioning the patient is not possible due to several factors including: the inability to reproduce the patient setup, i.e., the geometry and alignment of the patient's body; physiological changes in the patient, such as weight loss or tumor growth and shrinkage; and organ motions in the patients including but not limited to breathing motion, cardiac motion, rectal distension, peristalsis, bladder filling, and voluntary muscular motion. Note that the organ motions may occur on rapid time scales such that changes may occur during a single dose delivery (e.g., breathing motion), termed "intra-fraction" organ motions, or they may occur on slower time scales such that changes occur in between dose deliveries or surgical procedures, termed "inter-fraction" organ motions.

In both the fields of surgery and radiation therapy, patient setup errors, physiological changes, and organ motions result in increasing misalignment of the tracked surgical instrument or treatment beams relative to the anatomical targets and critical structures of a patient as the surgery or radiotherapy process proceeds.

For example, in the field of radiation therapy, for years practitioners have been acquiring hard-copy films of the patient using the radiation therapy beam, technically referred to as a "port film," to attempt to ensure that the beam position does not significantly vary from the original plan. However, the port films acquired are generally only single 2-D projection images taken at some predetermined interval during the radiotherapy process (typically 1 week). Port films cannot account for organ motion. Additionally, port films do not image soft tissue anatomy with any significant contrast, and only provide reliable information on the boney anatomy of the patient. Accordingly, misalignment information is only provided at the instants in time in which the port images are taken, and may be misleading as the boney anatomy and soft tissue anatomy alignment need not correlate and change with time. With appropriate markers in the port image provided, the beam misalignment may be determined and then corrected to some limited degree.

More recently, some have disclosed acquiring the port images electronically, referred to as electronic portal imaging. This imaging technique employs solid state semiconductor, scintillator, or liquid ionization chamber array technology to capture x-ray transmission radiographs of the patient using the x-rays of the linear accelerator or an associated kilovoltage x-ray unit. As with the hard-copy technique, misalignment data is only provided at the instants in time in which the port images are taken. Another recent advance in electronic portal imaging includes the use of implanted interstitial radio-opaque markers in an attempt to image the location of soft tissues. These procedures are invasive and subject to marker migration. Even when performed with the rapid acquisition of many images, these procedures only result in finding the motion of discrete points identified by the radio-opaque markers inside a soft tissue, and cannot account for the true complexities of organ motions and the dosimetric errors that they cause. Another recent advance involves the acquisition of a volumetric cone-beam x-ray CT image set or a helical tomotherapy megavoltage x-ray CT image set before or after a daily delivery of radiation therapy, where the image set can be used to create 3D volumetric image sets from the 2D electronic portal images. While this technology may account for some patient setup errors, such as the geometry and alignment of the patient's body, physiological changes in the patient, and inter-fraction organ motions in the patient, it cannot account for intra-fraction organ motions in the patients. Intrafraction organ motions are very important and include, but are not limited to, breathing motion, cardiac motion, rectal gas distension, peristalsis, bladder filling, and voluntary muscular motion.

Radiation therapy has historically been delivered to large regions of the body including the target volume. While some volume margin is required to account for the possibility of microscopic disease spread, much of the margin is required to account for uncertainties in treatment planning and delivery of radiation. Reducing the total volume of tissue irradiated is beneficial, since this reduces the amount of normal tissue irradiated and therefore reduces the overall toxicity to the patient from radiation therapy. Furthermore, reduction in overall treatment volume may allow dose escalation to the target, thus increasing the probability of tumor control.

Clinical cobalt ($^{60}$Co radioisotope source) therapy units and MV linear accelerators (or linacs) were introduced nearly contemporaneously in the early 1950's. The first two clinical cobalt therapy units were installed nearly simultaneously in October of 1951 in Saskatoon and London, Ontario. The first MV linear accelerator installed solely for clinical use was at Hammersmith Hospital in London, England, in June of 1952. The first patient was treated with this machine in August of 1953. These devices soon became widely employed in cancer therapy. The deeply penetrating ionizing photon beams quickly became the mainstay of radiation therapy, allowing the widespread noninvasive treatment of deep seated tumors. The role of X-ray therapy slowly changed with the advent of these devices from a mainly palliative therapy to a definitive curative therapy. Despite similarities, cobalt units and linacs were always viewed as rival technologies in external beam radiotherapy. This rivalry would result in the eventual dominance of linacs in the United States and Western Europe.

The cobalt unit was quite simplistic and was not technically improved significantly over time. Of course, the simplicity of the cobalt unit was a cause for some of its appeal; the cobalt units were very reliable, precise, and required little maintenance and technical expertise to run. Early on, this allowed cobalt therapy to become the most widespread form of external beam therapy.

The linac was the more technically intensive device. Linacs were capable of accelerating high currents of electrons to energies between 4 and 25 MeV to produce beams of bremsstrahlung photons or scattered electrons. As such, the linac was a much more versatile machine that allowed more penetrating beams with sharper penumbrae and higher dose rates. As the linac became more reliable, the benefits of having more penetrating photon beams coupled with the addition of electron beams was seen as strong enough impetus to replace the existing cobalt units.

Cobalt therapy did not die away without some protests, and the essence of this debate was captured in a famous paper in 1986 by Laughlin, Mohan, and Kutcher, which explained the pros and cons of cobalt units and linacs. This was accompanied by an editorial from Suit that pleaded for the continuance and further technical development of cobalt units. The pros of cobalt units and linacs have already been listed. The cons of cobalt units were seen as less penetrating depth dose, larger penumbra due to source size, large surface doses for large fields due to lower energy contamination electrons, and mandatory regulatory oversight. The cons for linacs increased with their increasing energy (and hence their difference from a low energy cobalt beam), and were seen to be increased builddown, increased penumbra due to electron transport, increased dose to bone (due to increased dose due to pair production), and most importantly the production of photoneutrons at acceleration potentials over 10 MV.

In the era before intensity modulated radiation therapy (IMRT), the linac held definite advantages over cobalt therapy. The fact that one could produce a very similar beam to cobalt using a 4 MV linac accelerating potential combined with the linac's ability to produce either electron beams or more penetrating photon beams, made the linac preferable. When the value of cobalt therapy was being weighed against the value linac therapy, radiation fields were only manually developed and were without the benefit of IMRT. As IMRT has developed, the use of higher MV linac accelerating potential beams and electron beams have been largely abandoned by the community. This is partly due to the increased concern over neutron production (and increased patient whole body dose) for the increased beam-on times required by IMRT and the complexity of optimizing electron beams, but most importantly because low MV photon-beam IMRT could produce treatment plans of excellent quality for all sites of cancer treatment.

IMRT represents a culmination of decades of improving 3D dose calculations and optimization to the point that we have achieved a high degree of accuracy and precision for static objects. However, there is a fundamental flaw in our currently accepted paradigm for dose modeling. The problem lies with the fact that patients are essentially dynamic deformable objects that we cannot and will not perfectly reposition for fractioned radiotherapy. Even for one dose delivery, intrafraction organ motion can cause significant errors. Despite this fact, the delivery of radiation therapy is traditionally planned on a static model of radiotherapy targets and critical structures. The real problem lies in the fact that outside of the cranium (i.e., excluding the treatment of CNS disease using Stereotactic radiotherapy) radiation therapy needs to be fractionated to be effective, i.e., it must be delivered in single 1.8 to 2.2 Gy fractions or double 1.2 to 1.5 Gy fractions daily, and is traditionally delivered during the work week (Monday through Friday), taking 7 to 8 weeks to deliver a curative dose of 70 to 72 Gy at 2.0 or 1.8 Gy, respectively. This daily fractionation requires the patient and all of their internal organs to be repositioned exactly for accurate dose delivery. This raises an extremely important question for radiation therapy: "Of what use is all of the elegant dose computation and optimization we have developed if the targets and critical structures move around during the actual therapy?" Recent critical reviews of organ motion studies have summarized the existing literature up to 2001 and have shown that the two most prevalent types of organ-motion: patient set-up errors and organ motions. While significant physiological changes in the patient do occur, e.g., significant tumor shrinkage in head-and-neck cancer is often observed clinically, they have not been well studied. Organ motion studies have been further subdivided into inter-fraction and intra-fraction organ motion, with the acknowledgement that the two cannot be explicitly separated, i.e., intra-fraction motions obviously confound the clean observation of inter-fraction motions. Data on inter-fraction motion of gynecological tumors, prostate, bladder, and rectum have been published, as well as data on the intra-fraction movement of the liver, diaphragm, kidneys, pancreas, lung tumors, and prostate. Many peer-reviewed publications, spanning the two decades prior to publication have demonstrated the fact that both inter- and intra-fraction organ motions may have a significant effect on radiation therapy dosimetry. This may be seen in the fact that displacements between 0.5 and 4.0 cm have been commonly observed in studies of less than 50 patients. The mean displacements for many observations of an organ motion may be small, but even an infrequent yet large displacement may significantly alter the biologically effective dose received by a patient, as it is well accepted that the correct dose per fraction must be maintained to effect tumor control. In a more focused review of intra-fraction organ motion recently published by Goitein (Seminar in Radiation Oncology 2004 January; 14(1):2-9), the importance of dealing with organ motion related dosimetry errors was concisely stated: "[I]t is incontestable that unacceptably, or at least undesirably, large motions may occur in some patients . . . ." It was further explained by Goitein that the problem of organ motions has always been a concern in radiation therapy: "We have known that patients move and breathe and that their hearts beat and their intestines wriggle since radiation was first used in cancer therapy. In not-so-distant decades, our solution was simply to watch all that motion on the simulator's fluoroscope and then set the field edge wires wide enough that the target (never mind that we could not see it) stayed within the field."

In an attempt to address the limitations imposed on radiation therapy by patient setup errors, physiological changes, and organ motion throughout the protracted weeks of radiation therapy, imaging systems have been introduced that are capable of acquiring a volumetric CT "snap shot" before and after each delivery of radiation. This combination of a radiation therapy unit with radiology imaging equipment has been termed image-guided radiation therapy (IGRT), or preferably image guided IMRT (IGIMRT). IGIMRT technology has the potential for removing patient setup errors, detecting slow physiological changes, and detecting inter-fraction organ motions that occur over the extended course of radiation therapy. However, IGIMRT technology cannot account for intra-fraction organ motion, which is a very significant form of organ motion. IGIMRT devices are only being used to shift the gross patient position. IGIMRT devices cannot capture intra-fraction organ motion and are limited by the speed at which helical or cone-beam CT imaging may be performed. Secondly, but perhaps equally important, CT imaging adds to the ionizing radiation dose delivered to the patient. It is well known that the incidence of secondary carcinogenesis occurs in regions of low-to-moderate dose, and the whole body dose will be increased by the application of many CT image studies.

CT imaging and MRI units were both demonstrated in the 1970's. CT imaging was adopted as the "gold standard" for radiation therapy imaging early on due to its intrinsic spatial integrity, which comes from the physical process of X-ray attenuation. Despite the possibility of spatial distortions occurring in MRI, it is still very attractive as an imaging modality for radiotherapy. MRI has a much better soft tissue contrast than CT imaging, and has the ability to image physiological and metabolic information, such as chemical tumor signals or oxygenation levels. The MRI artifacts that influence the spatial integrity of the data are related to undesired fluctuations in the magnetic field homogeneity and may be separated into two categories: 1) artifacts due to the scanner, such as field inhomogeneities intrinsic to the magnet design, and induced eddy currents due to gradient switching; and 2) artifacts due to the imaging subject, i.e., the intrinsic magnetic susceptibility of the patient. Modern MRI units are carefully characterized and employ reconstruction algorithms that may effectively eliminate artifacts due to the scanner. At high magnetic field strength, in the range of 1.0-3.0 T, magnetic susceptibility of the patient may produce significant distortions (which are proportional to field strength) that may often be eliminated by first acquiring susceptibility imaging data. Recently, many academic centers have started to employ MRI for radiation therapy treatment planning. Rather than dealing with patient-related artifacts at high field strength, many radiation therapy centers have employed low-field MRI units with 0.2-0.3 T for radiation therapy treatment planning, as these units diminish patient-susceptibility spatial distortions to insignificant levels. For dealing with intra-fraction organ motion, MRI is highly favorable due to the fact that it is fast enough to track patient motions in real-time, has an easily adjustable and orientable field of view, and does not deliver any additional ionizing radiation to the patient that may increase the incidence of secondary carcinogenesis. Breath-controlled and spirometer-gated fast multi-slice CT has recently been employed in an attempt to assess or model intra-fraction breathing motion by many research groups. Fast, single-slice MRI has also been employed in the assessment of intra-fraction motions, and dynamic parallel MRI is able to perform volumetric intra-fraction motion imaging. MRI holds a definite advantage over CT for fast repetitive imaging due to the need for CT imaging to deliver increasing doses to the patient. Concerns over increased secondary carcinogenesis due to whole-body dose already exist for IMRT and become significantly worse with the addition of repeated CT imaging.

Two research groups appear to have simultaneously been attempting to develop an MRI unit integrated with a linac. In 2001, U.S. Pat. No. 6,198,957 was issued to Green, which teaches an integrated MRI and linac device. In 2003, a group from the University of Utrecht in the Netherlands presented their design for an integrated MRI and linac device, and has since reported dosimetric computations to test the feasibility of their device. The significant difficulty with integrating an MRI unit with a linac, as opposed to a CT imaging unit, is that the magnetic field of the MRI unit makes the linac inoperable. It is well known that a charged particle moving at a velocity, $\vec{v}$, in the presence of a magnetic field, $\vec{B}$, experiences a Lorentz force given by $\vec{F}=q(\vec{v}\times\vec{B})$. The Lorentz force caused by the MRI unit will not allow electrons to be accelerated by the linac as they cannot travel in a linear path, effectively shutting the linac off. The high radiofrequency (RF) emittance of the linac will also cause problems with the RF transceiver system of the MRI unit, corrupting the signals required for image reconstruction and possibly destroying delicate circuitry. The integration of a linac with a MRI unit is a monumental engineering effort and has not previously been enabled.

Intensity modulated radiation therapy (IMRT) is a type of external beam treatment that is able to conform radiation to the size, shape, and location of a tumor. IMRT is a major improvement as compared to other conventional radiation treatments. The radiotherapy delivery method of IMRT is known in the art of radiation therapy and is described in a book by Steve Webb entitled "Intensity-Modulated Radiation Therapy" (IOP Publishing, 2001, ISBN 0750306998). This work of Webb is incorporated by reference into the application in its entirety and hereafter referred to as "Webb 2001." The effectiveness of conventional radiation therapy is limited by imperfect targeting of tumors and insufficient radiation dosing. Because of these limitations, conventional radiation may expose excessive amounts of healthy tissue to radiation, thus causing negative side-effects or complications. With IMRT, the optimal 3D dose distribution, as defined by criteria known in the art (such as disclosed by Webb 2001), is delivered to the tumor and dose to surrounding healthy tissue is minimized.

In a typical IMRT treatment procedure, the patient undergoes treatment planning x-ray CT imaging simulation with the possible addition of MRI simulation or a position emission tomography (PET) study to obtain metabolic information for disease targeting. When scanning takes place, the patient is immobilized in a manner consistent with treatment so that the imaging is completed with the highest degree of accuracy. A radiation oncologist or other affiliated health care professional typically analyzes these images and determines the 3D regions that need to be treated and 3D regions that need to be spared, such as critical structures, e.g. the spinal cord and surrounding organs. Based on this analysis, an IMRT treatment plan is developed using large-scale optimization.

IMRT relies on two advanced technologies. The first is inverse treatment planning. Through sophisticated algorithms using high speed computers, a treatment plan can be determined using an optimization process. The treatment plan is intended to deliver a prescribed uniform dose to a tumor while minimizing excessive exposure to surrounding healthy tissue. During inverse planning a large number (e.g. several thousands) of pencil beams or beamlets that comprise the radiation beam are independently targeted to the tumor or other target structures with high accuracy. Through optimization algorithms, the non-uniform intensity distributions of the individual beamlets are determined to attain certain specific clinical objectives.

The second technology relied on for IMRT involves the used of multi-leaf collimators (MLC). MLC technology allows for delivery of the treatment plan derived from the inverse treatment planning system. A separate optimization, referred to as leaf sequencing, is used to convert the set of beamlet fluences to an equivalent set of leaf motion instructions or static apertures with associated fluences. The MLC is typically composed of computer-controlled tungsten leaves that shift to form specific patterns, thereby blocking the radiation beams according to the intensity profile from the treatment plan. As an alternative to MLC delivery, an attenuating filter may also be designed to match the fluence of beamlets.

After the treatment plan is generated and quality control checking has been completed, the patient is immobilized and positioned on the treatment couch. Positioning of the patient includes attempting to reproduce the patient positioning from during the initial x-ray CT or magnetic resonance imaging. Radiation is then delivered to the patient via the MLC instructions or attenuation filter. This process is then repeated for many weeks until the prescribed cumulative dose is assumed to be delivered.

Magnetic resonance imaging (MRI) is an advanced diagnostic imaging procedure that creates detailed images of internal bodily structures without the use of ionizing radiation, which is used in x-ray or megavoltage x-ray CT imaging. The diagnostic imaging method of MRI is known in the arts of radiology and radiation therapy and is described in the books by E. M. Haacke, R. W. Brown, M. R. Thompson, R. Venkatesan entitled Magnetic Resonance Imaging: Physical Principles and Sequence Design (John Wiley & Sons, 1999, ISBN 0-471-35128-8) and by Z.-P. Liang and P. C. Lauterbur entitled Principles of Magnetic Resonance Imaging: A Signal Processing Perspective. (IEEE Press 2000, ISBN 0-7803-4723-4). These works of Haacke et al. and Liang and Lauterbur are incorporated herein by reference in their entirety, and are hereafter referred to as "Haacke et al. 1999" and "Liang and Lauterbur 2001," respectively. MRI is able to produce detailed images through the use of a powerful main magnet, magnetic field gradient system, radiofrequency (RF) transceiver system, and an image reconstruction computer system. Open Magnetic Resonance Imaging (Open MRI) is an advanced form of MRI diagnostic imaging that uses a main magnet geometry that does not completely enclose the patient during imaging. MRI is a very attractive imaging modality for radiotherapy as it has a much better soft tissue contrast than CT imaging and the ability to image physiological and metabolic information, such as spectroscopic chemical tumor signals or oxygenation levels. Many tracer agents exist and are under development for MRI to improve soft tissue contrast (e.g. Gadopentate dimeglumine for kidney or bowel enhancement, or Gadoterate meglumine for general contrast). Novel contrast agents are currently under development that will allow for the metabolic detection of tumors, similar to PET imaging, by employing either hyperpolarized liquids containing carbon 13, nitrogen 15, or similar stable isotopic agents or paramagnetic niosomes. All of these diagnostic MRI techniques enhance the accurate targeting of disease and help assess response to treatment in radiation therapy.

CT scanning for IMRT treatment planning is performed using thin sections (2-3 mm), sometimes after intravenous injection of an iodine-containing contrast medium. CT scanning has the advantage of being more widely available, cheaper than magnetic resonance imaging (MRI), and it may be calibrated to yield electron density information for treatment planning. Some patients who cannot be examined by MRI (due to claustrophobia, cardiac pacemaker, aneurism clips, etc.) may be scanned by CT.

The problem of patient setup errors, physiological changes, and organ motions during various medical treatments, including radiation treatment and IGS, is currently a topic of great interest and significance. For example, in the field of radiology, it is well known that the accuracy of conformal radiation therapy is significantly limited by changes in patient mass, location, orientation, articulated geometric configuration, and inter-fraction and intra-fraction organ motions (e.g. during respiration), both during a single delivery of dose (intrafraction changes, e.g., organ motions such as rectal distension by gas, bladder filling with urine, or thoracic breathing motion) and between daily dose deliveries (interfraction changes, e.g., physiological changes such as weight gain and tumor growth or shrinkage, and patient geometry changes). No single effective method has previously been known to account for all of these deviations simultaneously during each and every actual dose delivery. Current state-of-the-art imaging technology allows taking 2D and 3D megavoltage and orthovoltage x-ray CT "snap-shots" of patients before and after a medical treatment, or may allow for taking time-resolved 2D radiographs that have no soft tissue contrast during radiation delivery.

Great advances have been made in a number of medical fields that involve various types of medical therapies, including conformal radiation therapy and IGS. However, their true efficacy is not realized without improved real-time imaging guidance and control.

SUMMARY

The present disclosure includes detailed descriptions of embodiments that allow for real-time monitoring of patient anatomy during various types of medical treatments. For example, disclosed embodiments can include a device and/or a process for performing high temporal- and spatial-resolution magnetic resonance imaging (MRI) of the anatomy and target tissues of a patient during various forms of medical therapy, which can include, for example, radiation therapy and/or various types of surgical procedures.

According to one aspect of the present disclosure, a surgical guidance system can comprise a magnetic resonance imaging (MRI) system configured for generating MRI data representative of a portion of a patient, a planning interface for generating a surgical plan based at least in part on pre-surgical images and input information regarding surgical parameters for a surgical procedure, a control unit for receiving image data based on the MRI data acquired during the surgical procedure and for monitoring the image data for conditions included in the surgical parameters of the surgical plan, and an alert unit for issuing an alert based on instructions from the control unit, wherein the control unit is configured to instruct the alert unit to issue the alert based on detecting at least one of the conditions included in the surgical parameters of the surgical plan.

The MRI can include first and second main magnets separated by a gap. The MRI system can be configured for generating MRI data representative of the portion of the patient positioned in the gap.

The MRI can be configured such that images may be captured substantially simultaneously with performance of the surgical procedure. The control unit can be configured to employ the image data for monitoring patient's response to the surgical procedure substantially simultaneously with performance of the surgical procedure. The monitoring of the patient's response to the surgical procedure can include monitoring changes to the patient's anatomy substantially simultaneously with performance of the surgical procedure. The control unit can be configured to instruct the alert unit to issue the alert during the surgical procedure based on detecting at least one condition associated with the changes to the patient's anatomy.

The surgical guidance system can further comprise a tracking unit for tracking a surgical instrument used for performing the surgical procedure.

The surgical guidance system can further comprise a tracking unit for tracking a surgical robotic device performing the surgical procedure.

The alert unit can be configured to issue the alert in the form of at least one of visual information and audible information.

The surgical guidance system may further comprise an image processing unit for receiving the MRI data from the MRI system and generating image data based on the MRI data. The MRI system can be configured for obtaining MRI data representative of a first quality of images before the start of the surgical procedure, and for obtaining MRI data representative of a second quality of images during substantially simultaneous performance of the surgical procedure, the second quality being lower than the first quality. The image processing unit can be configured for generating image data representative of volumetric images from MRI data generated during the obtaining of MRI data representative of the second quality of images, wherein the generating of the image data representative of volumetric images can include using deformable image registration.

The image processing unit can be configured for generating image data representative of volumetric images based on the MRI data received from the MRI system. The image processing unit can be configured for generating the image data representative of volumetric images using deformable image registration.

According to another aspect of the present disclosure, a surgical guidance system can comprise an MRI system configured for generating MRI data representative of a portion of a patient substantially simultaneously with performance of a surgical procedure on the patient. The surgical guidance system can also comprise a control unit for receiving image data representative of volumetric images based on the MRI data acquired during the surgical procedure and for monitoring the image data for predetermined conditions, and an alert unit for issuing an alert based on instructions from the control unit. The control unit can be configured to instruct the alert unit to issue the alert based on detecting at least one of the predetermined conditions.

The surgical guidance system can further comprise a planning interface for receiving at least one of the predetermined conditions.

The MRI can be configured such that images may be captured substantially simultaneously with performance of the surgical procedure. The control unit can be configured to employ the image data for monitoring patient's response to the surgical procedure substantially simultaneously with performance of the surgical procedure. The monitoring of the patient's response to the surgical procedure can include monitoring changes to the patient's anatomy substantially simultaneously with performance of the surgical procedure.

The control unit can be configured to instruct the alert unit to issue the alert during the surgical procedure based on detecting at least one condition associated with the changes to the patient's anatomy.

The surgical guidance system can further comprise an image processing unit for receiving MRI data from the MRI system and generating image data representative of the volumetric images based on the MRI data. The MRI system can be configured for obtaining MRI data representative of a first quality of images before the start of the surgical procedure, and obtaining MRI data representative of a second quality of images during substantially simultaneous performance of the surgical procedure, the second quality being lower than the first quality. The image processing unit can be configured for generating image data representative of the volumetric images from MRI data generated during the obtaining of MRI data representative of the second quality of images, wherein the generating of the image data representative of volumetric images can include using deformable image registration.

The image processing unit can be configured for generating image data representative of the volumetric images using deformable image registration.

According to a further aspect of the present disclosure, a surgical guidance a surgical guidance method comprises generating MRI data representative of a portion of a patient; generating image data based on the MRI data; generating a surgical plan based at least in part on pre-surgical images and input information regarding surgical parameters for a surgical procedure; monitoring the image data for conditions included in the surgical parameters of the surgical plan; and issuing an alert based on detecting at least one of the conditions included in the surgical parameters of the surgical plan. The image data can be representative of volumetric images based on the MRI data.

These and other features, aspects, and embodiments are described below in the section entitled "Detailed Description of the Drawings."

BRIEF DESCRIPTION OF DRAWINGS

There are shown in the drawings, embodiments which are presently contemplated, it being understood, however, that the present disclosure is not limited to the precise arrangements and instrumentalities shown.

FIG. 8 shows axial dose distributions from a single head-and-neck IMRT case planned using commissioned cobalt beamlets;

FIG. 9 shows DVH data derived from the single head-and-neck IMRT case shown in FIG. 8;

FIG. 12 shows cobalt beamlets dose distributions in water and air with and without a 0.3 Tesla magnetic field;

DETAILED DESCRIPTION OF THE DRAWINGS

Figure 1:
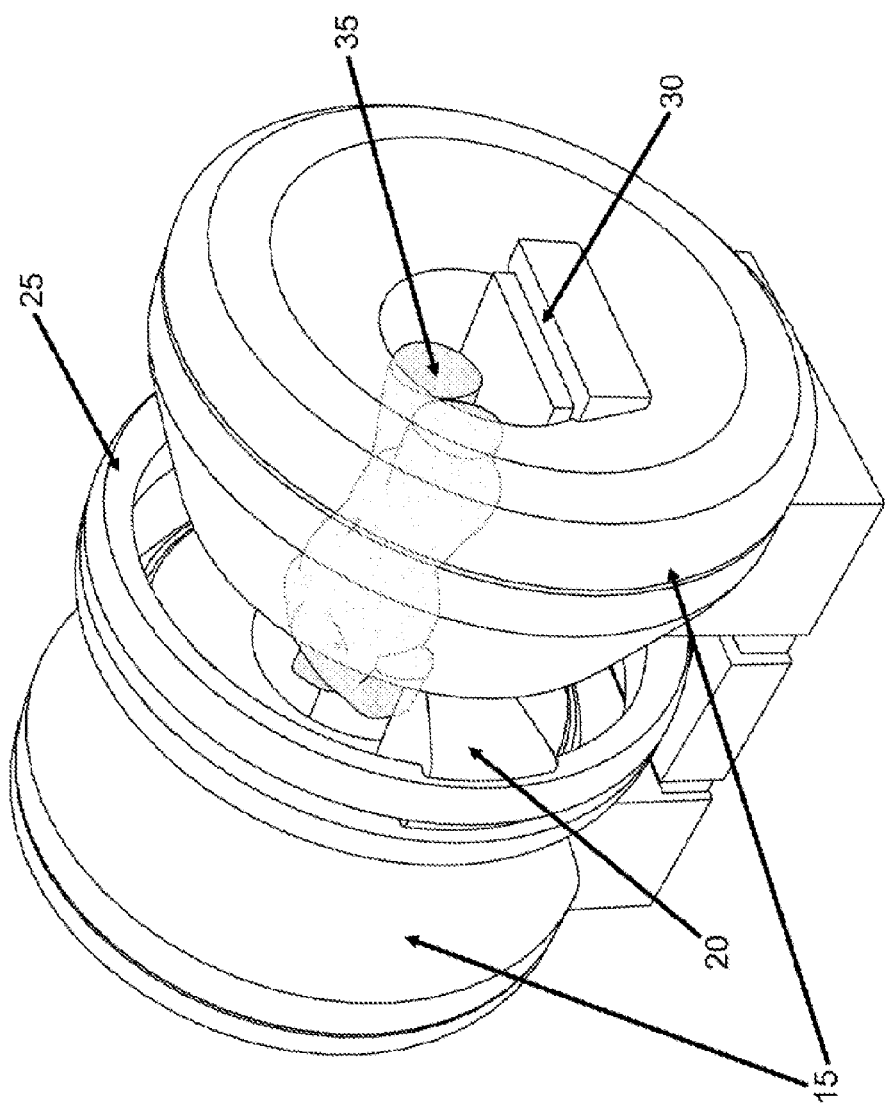
FIG. 1 shows a schematic view of a radiation therapy system according to the present disclosure.

Aspects of the present disclosure are more particularly described in the following examples that are intended to be illustrative only since numerous modifications and variations therein will be apparent to those skilled in the art. As used in the specification and in the claims, the singular form "a," "an," and "the" may include plural referents unless the context clearly dictates otherwise.

The present disclosure includes detailed descriptions of embodiments that allow for real-time monitoring of patient anatomy during various types of medical treatments. For example, disclosed embodiments can include a device and/or a process for performing high temporal- and spatial-resolution magnetic resonance imaging (MRI) of the anatomy and disease of a patient during various forms of medical therapy, which can include, for example, radiation therapy and/or various types of surgical procedures. Specific, non-limiting embodiments disclosed herein include embodiments that include radiation therapy systems and embodiments that include surgical guidance systems.

Thus, according to some embodiments, a radiation therapy device and a process are provided for performing high temporal- and spatial-resolution MRI of the anatomy and disease of a patient during intensity modulated radiation therapy (IMRT) to directly measure and control the highly conformal ionizing radiation dose delivered to the patient. In a beneficial embodiment, a radiation therapy system comprises an open MRI that allows for axial access with IMRT radiation beams to the patient, a multileaf-collimator or compensating filter-based IMRT delivery system, and cobalt-60 teletherapy radiation source or sources in a single co-registered and gantry-mounted system.

As mentioned, prior systems do not simultaneously image the internal soft tissue anatomy of a person in real time during the delivery of radiation therapy while the radiation beams are striking the patient. Rather, in prior systems, an image is generated prior to and/or after the radiation delivery, and these images do not reflect any movement and/or natural changes that may occur in the patient during radiation delivery. As such, targeted radiation without the devices described here may not be successful if, after taking an initial image, the portion of the body to be treated either changes in size naturally, or changes in location due to the shifting of the patient prior to treatment; i.e., the occurrence of patient setup errors or errors in the geometry and alignment of the patients anatomy; physiological changes in the patient, such as weight loss or tumor growth and shrinkage; and organ motions in the patient including, but not limited to, breathing motion, cardiac motion, rectal distension, peristalsis, bladder filling, and voluntary muscular motion.

Aspects of the present disclosure allow for a system and method that help to eliminate problems of prior systems by allowing for real-time MRI of the patient substantially simultaneous to radiation delivery. The targeted radiation can be readjusted if the region to be treated suffers from any type of dosimetric error caused patient setup error, physiological change, and/or inter-fraction or intra-fraction organ motion. Many actions may be taken including, but not limited to: shifting the patient position to account for changes in size and/or position of targets and anatomy; stopping treatment altogether to permit additional calculations to be determined before restarting treatment or allow for the cessation of transitory motion; adding extra delivery fractions to increase the probability of tumor control or limiting the number of delivery fractions to decrease the probability of side effect; any of the beneficial process embodiments previous described; and reoptimizing the IMRT treatment plan on a variety of time scales, e.g., reoptimization for every delivery, every beam, or every segment in the IMRT plan is performed.

Real-time imaging as referred to herein can refer to repetitive imaging that may be acquired fast enough to capture and resolve any intra-fraction organ motions that occur and that can result in significant changes in patient geometry during a medical treatment, for example while a dose of radiation is being delivered. The data obtained by real-time imaging can allow for the determination of the actual dose deposition in the patient. This can be achieved by applying known techniques of deformable image registration and interpolation to sum the doses delivered to the moving tissues and targets. This data can be collected over the course of an entire multi-session radiotherapy treatment program, where data is accumulated while the radiation beams are striking the patient and delivering the radiation dose, thereby allowing for the quantitative determination of 3D in vivo dosimetry. Hence, the present disclosure enables an effective means of assessing and controlling, or eliminating, organ-motion related dose-delivery errors.

Reference is now made with specific detail to the drawings in which like reference numerals designate like or equivalent elements throughout the several views, and initially to FIG. 1.

In FIG. 1, an embodiment of the present disclosure includes an open MRI 15 and an IMRT cobalt therapy unit 20. The system shown in FIG. 1 also includes a means to perform IMRT in the IMRT cobalt therapy unit 20, such as an MLC or compensation filter unit, and a gantry 25 that may be used for rotating the IMRT cobalt therapy unit 20 while keeping the MRI 15 stationary. A patient 35 is positioned on an adjustable, stationary couch 30.

Figure 2:
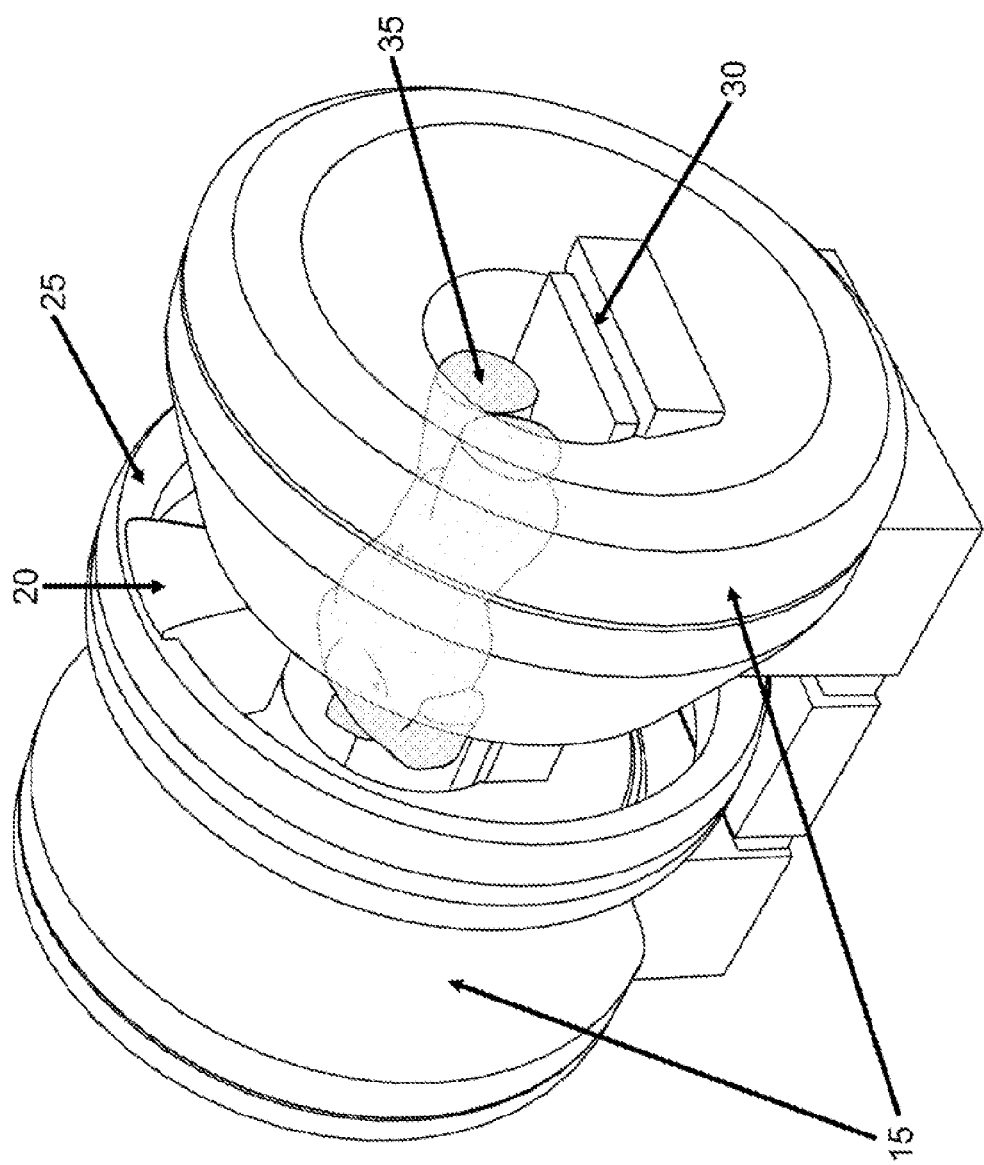
FIG. 2 shows another schematic view of the radiation therapy system shown in FIG. 1, where a radiation source and collimator have been rotated from the position shown in FIG. 1.
Figure 3:
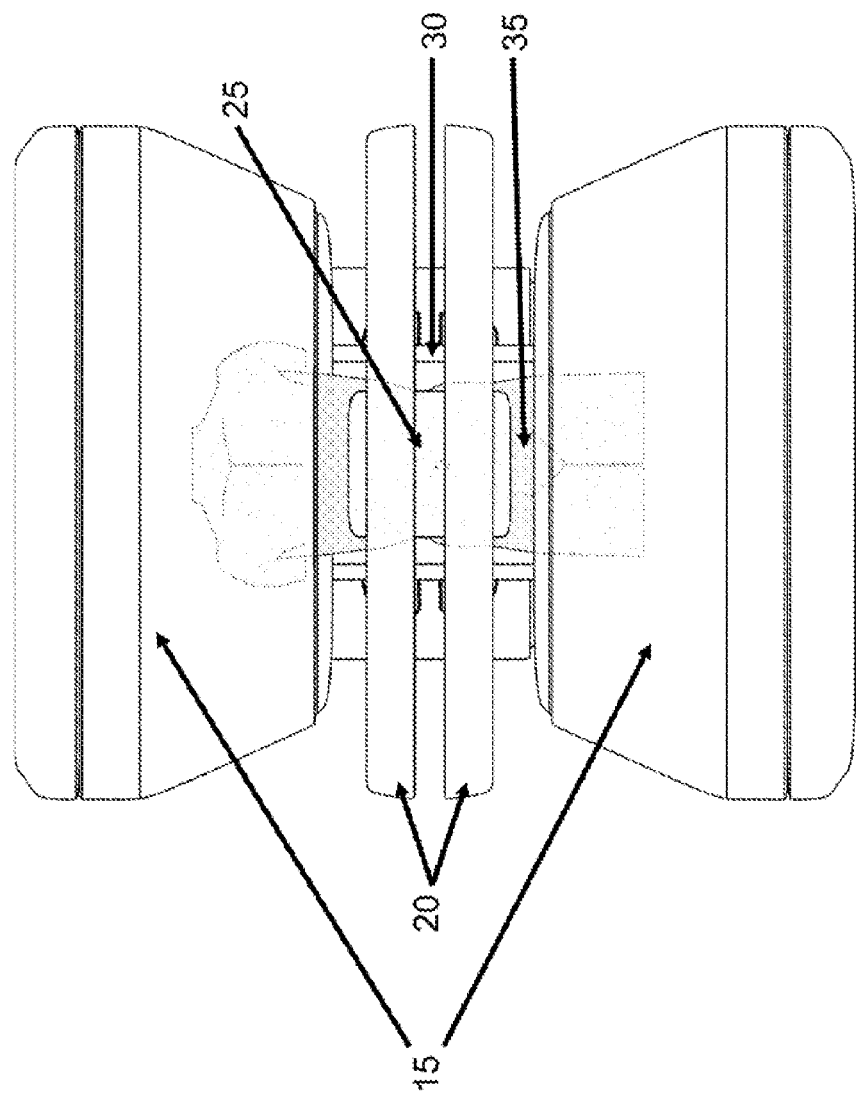
FIG. 3 shows a top view of the radiation therapy system shown in FIG. 1.
Figure 4:
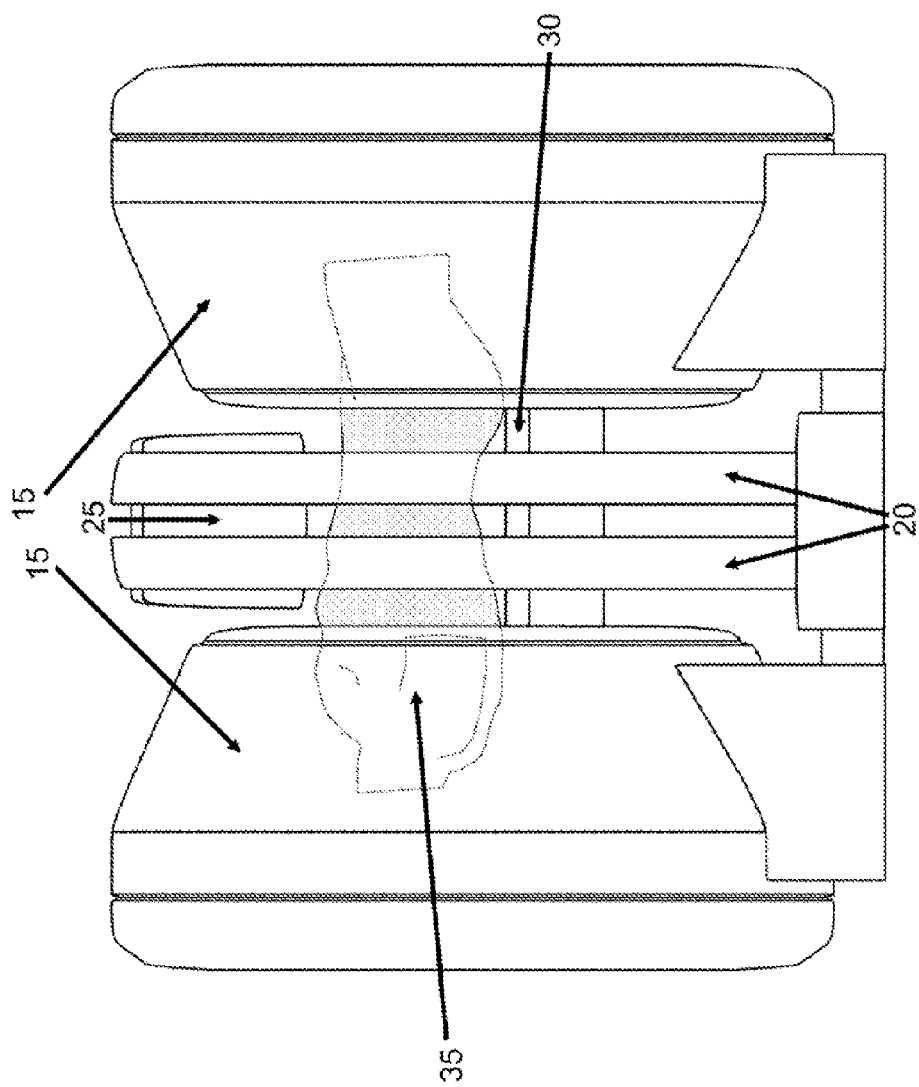
FIG. 4 shows a side view of the radiation therapy system shown in FIG. 1.

FIG. 2 shows the system in use, and where the gantry 25 has been rotated approximately 90 degrees clockwise relative to its position in FIG. 1. As such, the IMRT cobalt therapy unit 20 is in position to treat the patient 35 in one of many selectable locations. FIG. 3 shows a top view of the system shown in FIG. 1, and FIG. 4 shows a side view of the system shown in FIG. 1.

Figure 5:
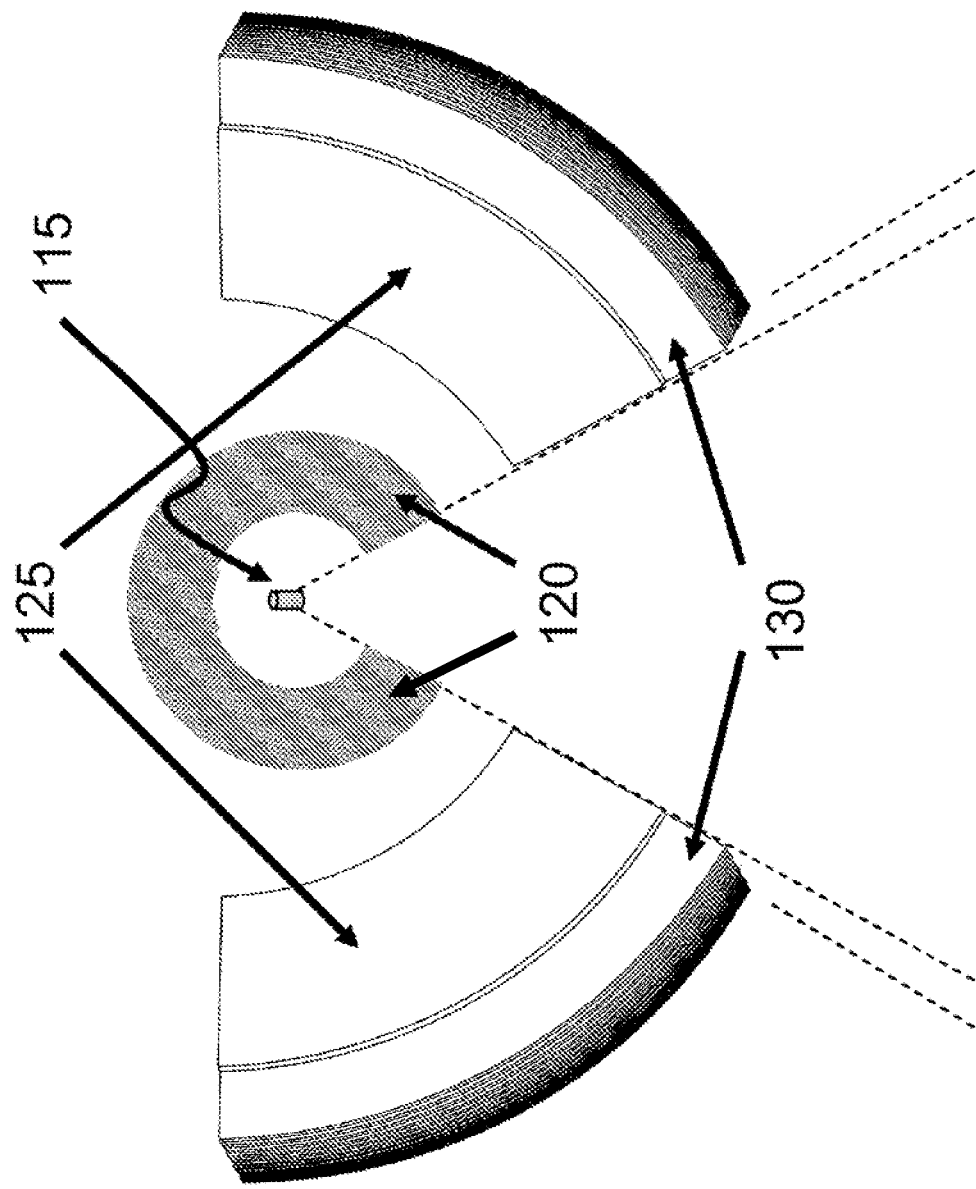
FIG. 5 shows a detailed schematic view of the co-registered isotopic radiation source of the radiation therapy system shown in FIG. 1.
Figure 6:
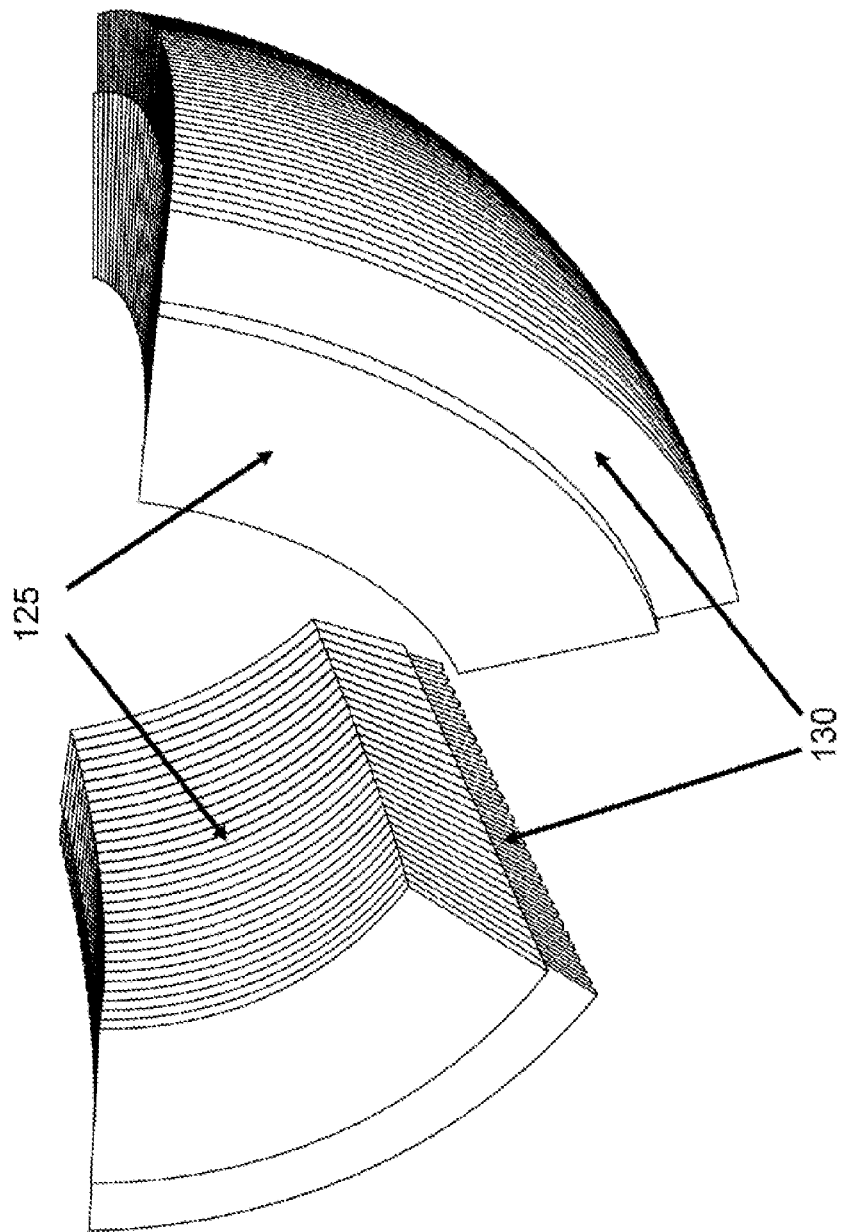
FIG. 6 shows a perspective view of collimators of the radiation therapy system shown in FIG. 1.
Figure 7:
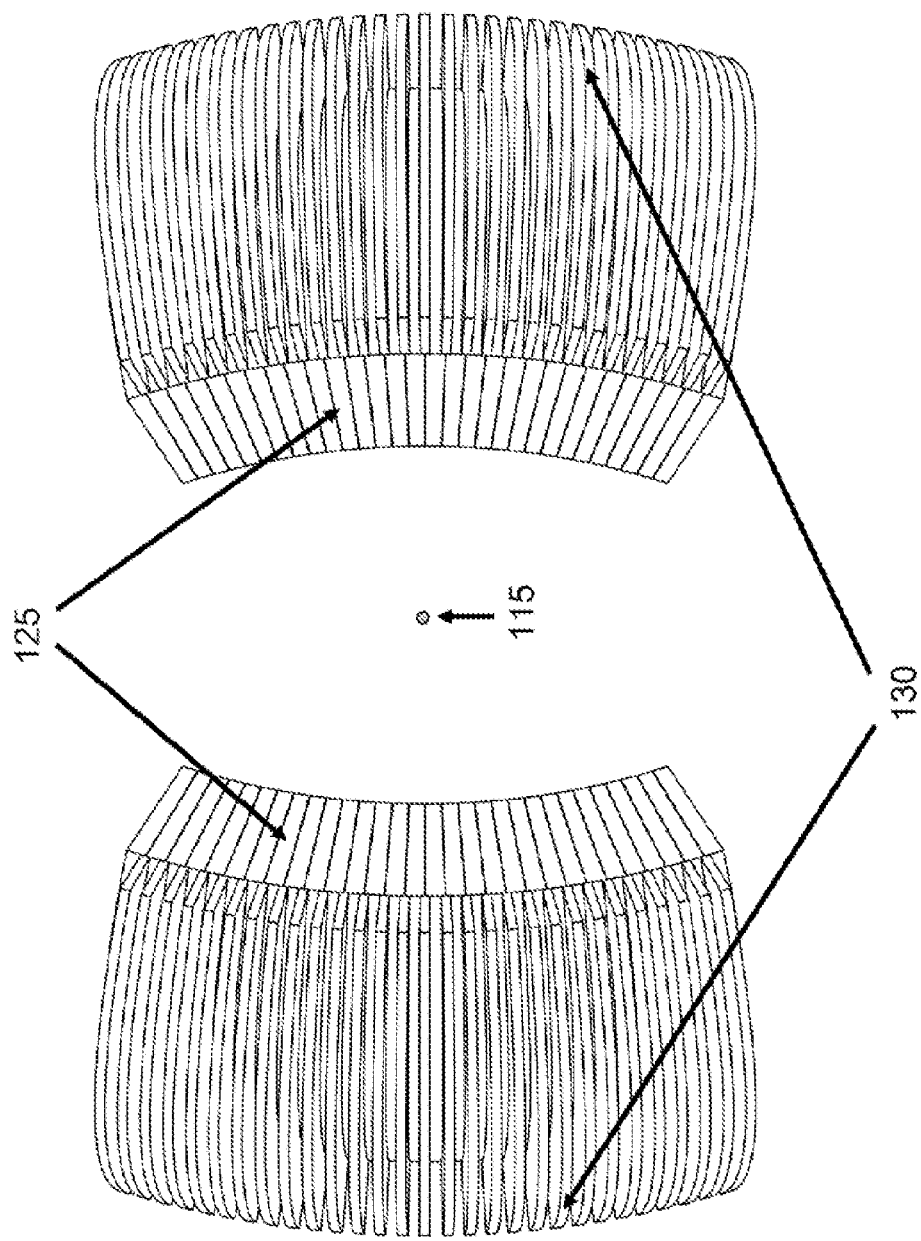
FIG. 7 shows a beams-eye view of the radioisotopic source and collimators of the radiation therapy system shown in FIG. 1.

FIG. 5 shows a detailed schematic view of a co-registered isotopic radiation source with a multi-leaf collimator, which serves as an embodiment of the IMRT cobalt therapy unit in FIG. 1. A radioisotopic source 115 is shown with a fixed primary collimator 120, a secondary doubly-divergent multileaf collimator 125, and a tertiary multi-leaf collimator 130 for blocking interleaf leakage from the secondary multi-leaf collimator 125. FIG. 6 shows a perspective view of the secondary doubly-divergent multi-leaf collimator 125 and the tertiary multi-leaf collimator 130. As mentioned, the tertiary multi-leaf collimator 130 is provided for blocking interleaf leakage from the secondary multi-leaf collimator 125. FIG. 7 shows a beams-eye view of the radioisotopic source 115, the secondary doubly divergent multi-leaf collimator 125, and the tertiary multi-leaf collimator 130.

A beneficial embodiment of the present disclosure can thus include a computer-controlled cone-beam cobalt therapy unit 20, such as a cobalt-60 therapy unit, equipped with a multileaf collimator or an automated compensating filter system mounted on a rotational gantry 25 along with an orthogonally mounted "Open" MRI unit 15. The IMRT cobalt unit 20 projects its cone-beam geometry radiation down the center of the opening of the axial open MRI unit 15. The IMRT cobalt unit 15 rotates on a gantry 25 axially (about the longitudinal (cranial-caudal) axis of the patient) about a patient 35. An adjustable treatment couch 30 may be used to support the patient 35 in a stationary position while the gantry 25 rotates to change the beam angle.

The present embodiment can use cobalt teletherapy as the radiation therapy. While some IMRT use a linear electron accelerator for delivering a more penetrating radiation therapy, the accelerator itself produces a treatment beam that is highly variable in regards to the level of radiation emitted. As such, it becomes difficult to accurately determine the amount of radiation that is being used on the patient and to coordinate the motion of an MLC for IMRT delivery. Gamma-rays are electromagnetic radiation emitted by the disintegration of a radioactive isotope and have enough energy to produce ionization in matter, typically from about 100 keV to well over 1 MeV. The most useful gamma-emitting radioactive isotopes for radiological purposes are found to be cobalt (Co 60), iridium (Ir 192), cesium (Cs 137), ytterbium (Yb 169), and thulium (Tm 170). As such, the disintegration of a radioactive isotope is a well-known phenomena and, therefore, the radiation emitted by cobalt teletherapy is more consistent and, therefore, easier to calculate in terms of preparing a treatment regimen for a patient.

Enablement of the present embodiment's cobalt IMRT has been demonstrated via computational analysis. Simulations have been performed of IMRT delivery with a commercially available cobalt therapy unit and a MLC. A 3D image-based radiation therapy treatment planning system with a cobalt beamlet model was commissioned and validated using measured radiochromic film data from a Theratronics 1000C cobalt therapy unit. An isotropic 4×4×4 $mm^3$ dose voxel grid (effectively Shannon-Nyquist limited for γ-ray IMRT source penumbra) was generated. This beamlet model was fitted to published data and validated with radiochromic film measurements of 1×1 $cm^2$ beamlets formed by a Cerrobend block and measured using a previously reported methodology. The calculation depths were then determined for the same voxels with standard three-dimensional ray-tracing of the structures. Density scaling to the depths computed was used to better account for tissue heterogeneities in the dose model. The CPLEX, ILOG Concert Technologies industrial optimization solver using an implementation of the barrier interior-point method with dense column handling for IMRT optimization was used to solve for optimal IMRT plans. Beamlet fluences were discretized for each beam angle to 5% levels for leaf sequencing. The resulting plan dose distribution and histograms were computed by summing the dose values weighted by the deliverable discretized intensities. Leaf-transmission leakage intensities were conservatively estimated at 1.7% for otherwise zero intensity beamlets. Finally, standard methods of heuristic leaf-sequencing optimization to create delivery instructions for the treatment plans were employed. We adopted the Virginia Medical College simultaneous integrated boost (SIB) target dose-level scheme as it is the largest maximum to minimum clinical prescription dose ratio advocated in the literature, making it the most difficult dose prescription scheme to satisfy. Head-and-neck IMRT provides an excellent basis for testing IMRT optimization for several reasons: 1) there are well defined treatment goals of sparing salivary glands and other structures while maintaining homogeneous target coverage; 2) attempting to achieve these goals tests IMRT optimization to its technical limits; and 3) a large phase I/II multi-institutional trial, the Radiation Therapy Oncology Group (RTOG)'s H-0022 *Phase I/II Study of Conformal and Intensity Modulated Irradiation for Oropharyngeal Cancer*, has defined a common set of planning criteria. The case examined was run with 7 equispaced beams having International Electrotechnical Commission (IEC) gantry angles of 0°, 51°, 103°, 154°, 206°, 257°, and 309°. The treatment planning system generated 1,289 beamlets to adequately cover the targets from the seven beam angles, and the 4 mm isotropic voxel grid generated 417,560 voxels. FIG. 8 and FIG. 9 show results of the treatment. Note that our system normalized plans to ensure 95% coverage of the high dose target. FIG. 8 shows axial dose distributions from the single head-and-neck IMRT case planned using the commissioned cobalt beamlets. Excellent target coverage and tissue sparing may be observed. FIG. 9 shows the DVH data derived from the leaf sequenced and leakage corrected plan (i.e., deliverable plan) using the 4 mm voxels and 1 Gy dose bins. The cobalt source based IMRT created an excellent IMRT treatment plan for a head-and-neck patient. The γ-ray IMRT was able to clearly spare the right parotid gland (RPG) and keep the left parotid (LPG) and right submandibular glands (RSMG) under 50% volume at 30 Gy, while covering more than 95% of the target volumes (CTV and GTV) with the prescription dose or higher. All other structures were below tolerance. The unspecified tissue (SKIN) was kept below 60 Gy, with less than 3% of the volume above 50 Gy. The optimization model used was the same as published in Romeijn et al. and was not modified for the cobalt beams. For sites with larger depths such as prostate and lung it is known in the art that the addition of extra beams or isocenters allows for the creation of treatment plans using cobalt IMRT that may achieve the same clinical quality criteria as linac-based IMRT. This enabling demonstration shows that a cobalt therapy unit is capable of providing high quality IMRT.

Figure 10:
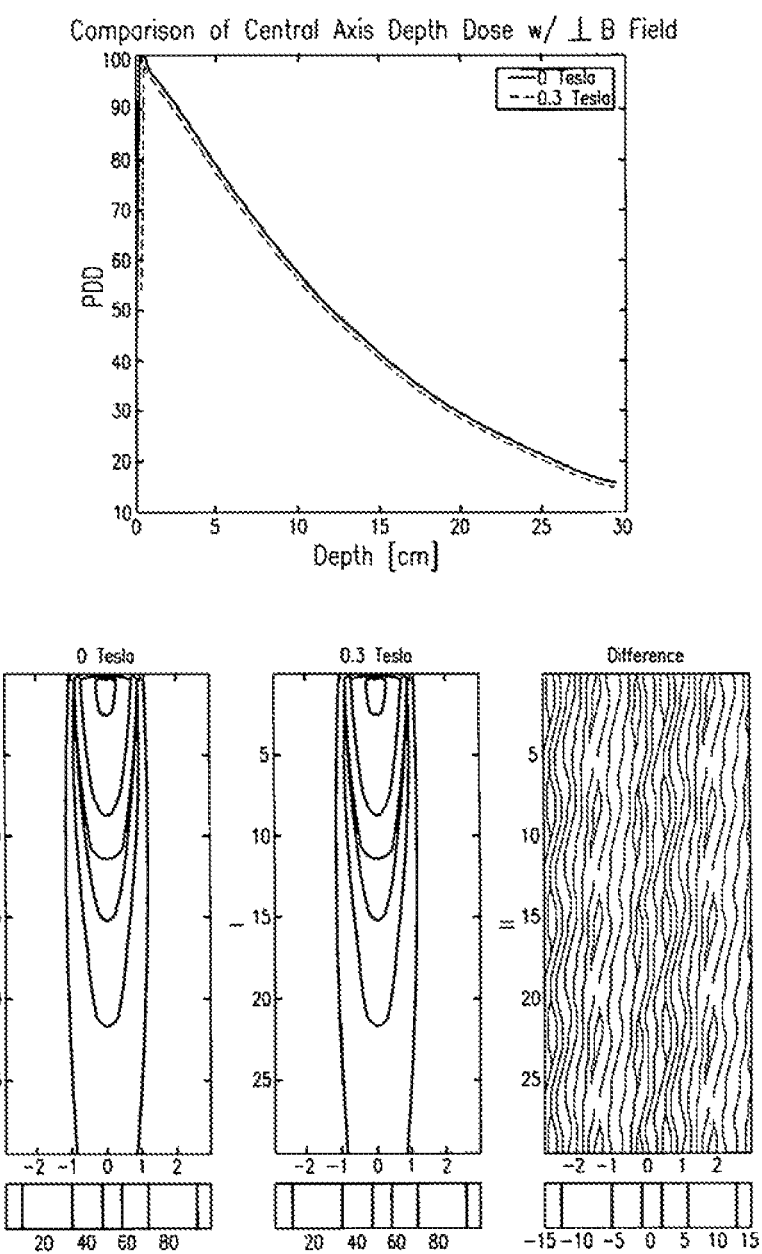
FIG. 10 shows cobalt beamlet dose distributions in water with and without a 0.3 Tesla magnetic field.
Figure 11:
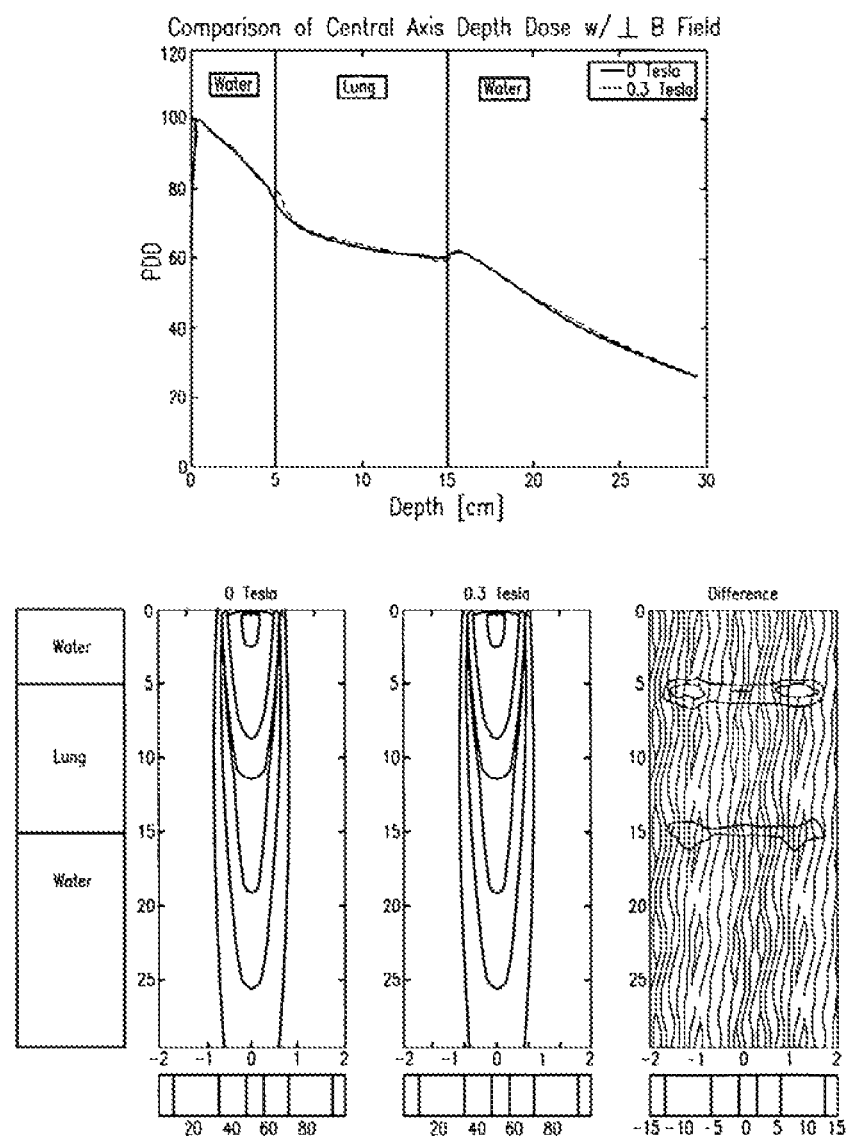
FIG. 11 shows cobalt beamlets dose distributions in water and lungs with and without a 0.3 Tesla magnetic field.

Enablement of the present embodiment's dose computation for cobalt IMRT in the presence of the magnetic field has been demonstrated via computational analysis. In addition, by using cobalt teletherapy, better calculations can be made based upon the magnetic field of the MRI. When the radiation therapy is performed while the patient is stationed within the MRI, the magnetic field will cause a slight deflection of the targeted radiation. As such, the calculations used to determine the treatment regimen need to take this deflection into account. A charged particle moving in a vacuum at a velocity, $\bar{v}$, in the presence of a magnetic field, $\bar{B}$, experiences a Lorentz force given by $F=q(\bar{v}\times\bar{B})$. This force is not significant enough to significantly change the physics of the interactions of ionizing photons and electrons with matter; however, it may influence the overall transport of ionizing electrons and hence the resulting dose distribution. The impact of magnetic fields on the transport of secondary electrons has been well studied in the physics literature, starting more than 50 years ago. Recent studies have employed Monte Carlo simulation and analytic analysis in an attempt to use a localized magnetic field to help focus or trap primary or secondary electrons to increase the local dose deposition in the patient. All of these studies have examined aligning the direction of the magnetic field lines along the direction of the beam axis to laterally confine the electron transport with the Lorentz force (called "longitudinal" magnetic fields, where the term longitudinal refers to the beam and not the patient). For high field MRI, with magnetic fields between about 1.5-3.0 T is known that the initial radius of gyration is small with respect to the MFP of large-angle scattering interactions for the secondary electrons (bremsstrahlung, elastic scatter, and hard collisions) and this condition results in the desired trapping or focusing of the electrons. As the electrons lose energy the radius decreases as it is proportional to $|\bar{v}|$ and, in the absence of large-angle scattering interactions (CSDA) the electrons would follow a spiral with decreasing radius until they stop. Although this spiraling may change the fluence of electrons it is known that it does not produce any significant synchrotron radiation. In the present embodiment, the magnetic field is preferably orthogonal to the radiation beams in order allow parallel MRI for real-time imaging. Recent work has shown that a 1.5 T magnetic field perpendicular to the beam axis of a 6 MV linac beam may significantly perturb the dose distribution to water for a 6 MV linac beamlet. Both to avoid such dose distribution distortions and to prevent MRI artifacts that could compromise the spatial integrity of the imaging data, a beneficial embodiment of the present disclosure uses a low field open MRI design that allows the magnetic field to be directed along the superior-inferior direction of the patient (see FIG. 1). Simple estimates of the radii of gyration for secondary electrons from cobalt γ rays indicate that the radii of gyration are much greater than the MFP for large-angle scattering interactions for electrons. This is easily understood as the Lorentz force is proportional to the magnitude of the magnetic field, $|\overline{B}|$ and the radius of gyration is inversely proportional to the magnetic field. We have pursued modeling a beamlet from a cobalt γ-ray source in a slab phantom geometry using the well-validated Integrated Tiger Series (ITS) Monte Carlo package and its ACCEPTM subroutine for transport in magnetic fields. For the simulations we employed 0.1 MeV electron and 0.01 MeV photon transport energy cutoffs, the standard condensed history energy grid (ETRAN approach), energy straggling sampled from Landau distributions, mass-collisional stopping powers based on Bethe theory, default electron transport substep sizes, and incoherent scattering including binding effect. Three pairs of simulations were run where each pair included the run with and without a 0.3 T uniform magnetic field parallel to the beam direction. A 2 cm circular cobalt γ-ray beamlet was modeled on the following geometries: a 30×30×30 cm$^3$ water phantom; a 30×30×30 cm$^3$ water phantom with a 10 cm lung density (0.2 g/cc) water slab at 5 cm depth; and a 30×30×30 cm$^3$ water phantom with a 10 cm air density (0.002 g/cc) water slab at 5 cm depth. Simulations were run with between 30 and 100 million histories on a P4 1.7 GHz PC for between 8 and 30 hours to obtain less than a percent standard deviation in the estimated doses. The results are displayed in FIGS. 10-12. FIG. 10 clearly demonstrates that a 0.3 T perpendicular uniform magnetic field, as would exist in a beneficial embodiment of the current disclosure, will not measurably perturb the dose distribution in soft tissue or bone. A very useful treatment site for the present embodiment will be lung and thorax, which contain the most significant tissue heterogeneities in the body. As seen in FIG. 11, adding a 12 cm lung density (0.2 g/cc) water slab to the phantom causes a very small yet detectable perturbation in the dose at the interfaces of the high and low density regions. These perturbations are small enough to allow acceptable clinical application without correction. In FIG. 12, we finally observe significant perturbations, which exist largely in the low-density and interface regions. This demonstrates that air cavities will hold the greatest challenge for accurate dosimetry. However, other than at interfaces with lower density media there should be no significant perturbations in soft tissue and bone (where the MFP shortens even more than soft tissue). This data demonstrates that in a beneficial embodiment of the present disclosure with a low (0.2-0.5 Tesla) field MRI, dose perturbation will be small except inside of air cavities were accurate dosimetry is not required due to an absence of tissue. By using a known radiation source, such as a cobalt teletherapy unit, the amount of deflection may be easily determined if the strength of the MRI field is known. However, even if the strength of the field is known, if a linear accelerator is used, the unknown energy spectrum of the radiation makes the calculations much more difficult.

Alternate sources of radiation that do not interfere significantly with the operations of the MRI unit such as protons, heavy ions, and neutrons that are produced by an accelerator or reactor away from the MRI unit and transported by beam to patient can also be included in alternative embodiments.

In addition, the strength of the MRI field will factor into the calculations and, as a result, the use of open MRIs offers advantages over closed MRIs. In an open MRI, the strength of the field generated is generally less than the field of a closed MRI. As such, the images resulting from an open MRI have more noise and are not as clear and/or defined as images from a higher field closed MRI. However, the stronger field of the closed MRI causes more of a deflection of the radiation treatment than the weaker field of an open MRI. Accordingly, depending on the characteristics most beneficial to a given treatment regimen, a closed MRI could alternatively be used. However, due to ease of calculation and/or the fact that a slightly less clear image during treatment is sufficient for adjusting most treatment regimens, an open MRI of the geometry shown in FIG. 1 is preferably used with the cobalt teletherapy to eliminate significant dose perturbations, prevent spatial imaging distortions, and allow for fast parallel phased array MRI.

By using an open MRI and cobalt teletherapy, three dimensional (3D) imaging of a patient can be accomplished during the radiation therapy. As such, by using the 3D images of the target region and the planning images of the target region, a displacement can be determined that can be updated based upon the continuous 3D images received during the radiotherapy process. Using the information obtained, the patient may then be then translated relative to the treatment beam to reduce the displacement during the irradiation process, such as if the measured displacement is outside a predetermined limit. Irradiation may then continue after translation. Alternatively, the treatment beam may be moved. The translation may occur during treatment or treatment may be stopped and then translation may occur.

By using 3D images during treatment and using these images to rapidly position and/or adjust the patient during the radiotherapy process, treatment accuracy may be substantially improved. If the patient becomes misaligned while radiation is being applied, the misalignment may be mitigated through positional adjustment. In addition to possible dose escalation, improved positional accuracy permits treatment of tumors that are currently considered not treatable with radiation using conventional systems. For example, primary spinal cord tumors and spinal cord metastases are typically not treated by conventional radiation systems due to the high accuracy needed to treat lesions in such important functional anatomic regions. The increased precision provided by 3D imaging during treatment makes it feasible to treat these types of tumors. Improvements are also expected for targets located in the lung, upper thorax, and other regions where intra-fraction organ motions are known to cause problems with radiotherapy dosimetry.

In an alternative embodiment, a separate guidance system can be used to track the patient location. The guidance system can be used to correlate the actual patient position with the imaging information obtained during both planning and radiotherapy. This may significantly improve the ease of patient positioning by providing updateable image correlation and positioning information throughout the patient set-up and treatment delivery phases, even when the patient is moved to positions that are not perpendicular to the coordinate system of the therapy machine. This ability to monitor patient position at non-coplanar treatment positions may be a significant improvement over conventional radiotherapy systems. In one beneficial embodiment, the guidance system may include an adjustable bed or couch for the patient to be placed upon. In an alternative beneficial embodiment, the guidance system may include a gantry that permits substantially simultaneous movement of the MRI and the cobalt therapy unit. Some beneficial embodiments include both the gantry and the adjustable bed or couch.

The initial radiation treatment and/or any changes to the treatment regimen can be determined based upon the use of a computer program that takes into account various factors including, but not limited to, the area of the patient to be treated, the strength of the radiation, the strength of the MRI field, the position of the patient relative to the radiation unit, any change in the patient during treatment, and/or any positional changes necessary of the patient and/or the radiation unit during treatment. The resulting IMRT is then programmed and the treatment is started.

One embodiment for determining a treatment plan for intensity modulated radiation treatment (IMRT) includes dividing a three dimensional volume of a patient into a grid of dose voxels, wherein each dose voxel is to receive a prescribed dose of radiation from a plurality of beamlets each having a beamlet intensity, and providing a convex programming model with a convex objective function to optimize radiation delivery. The model is solved to obtain a globally optimal fluence map, the fluence map including beamlet intensities for each of the plurality of beamlets. This method is described in greater detail in U.S. Patent Application Publication No. 2005/0207531, filed Jan. 20, 2005, titled "RADIATION THERAPY SYSTEM USING INTERIOR-POINT METHODS AND CONVEX MODELS FOR INTENSITY MODULATED FLUENCE MAP OPTIMIZATION," which is hereby incorporated herein by reference.

In general, the method used for determining a treatment plan, in one beneficial embodiment, is the interior point method and variants thereof. This method is beneficial due to its high efficiency and resulting generally short computational times. The interior point method is described in a book by Steven J. Wright entitled "Primal-Dual Interior-Point Methods" (SIAM, Publications, 1997, ISBN 089871382X). Primal-dual algorithms have emerged as the most beneficial and useful algorithms from the interior-point class. Wright discloses the major primal-dual algorithms for linear programming, including path-following algorithms (short- and long-step, predictor-corrector), potential-reduction algorithms, and infeasible-interior-point algorithms.

Once the treatment plan is determined, the clinician is able to ensure that the treatment plan is followed. The patient to be treated is placed in the MRI. An image of the area to be treated is taken and the MRI continues to transmit a 3D image of the area. The treatment plan is input into the cobalt radiation teletherapy unit and treatment commences. During treatment, a continuous image of the area being treated is observed. If the location of the area to be treated changes, such as if the patient moves or the area to be treated changes in size, the treatment plan is recalculated and/or the patient or radiation unit is adjusted without interrupting treatment. Alternatively, treatment can be stopped, then the treatment plan can be recalculated, and then the position of the patient and/or the radiation unit can be readjusted before recommencing treatment.

Multiple process embodiments may be used in improving the accuracy of the patient's therapy. One process embodiment can include taking the MRI data and applying methods known in the art for deformable image registration and dose calculation to the delivered IMRT cobalt unit fluences to determine the dose delivered to the target and critical structures during each delivery fraction. Corrections to the patient's treatment could then be taken to add or subtract delivery fractions to improve tumor control or reduce side effects, respectively. Along with the dosimetric assessment, the size and progression of the patient's disease would also be assessed on a daily basis.

A second process embodiment can include taking the MRI data and performing a reoptimization of the IMRT treatment plan before each single radiation delivery to improve the accuracy of the treatment delivery. This process can be combined with the previous process to assess the dose delivered to the target and critical structures during each delivery fraction.

A third process embodiment can include taking the MRI data and performing a reoptimization of the IMRT treatment plan on a beam-by-beam basis before the delivery of each radiation beam in a single radiation delivery to improve the accuracy of the treatment delivery. This process can include that the first process be performed rapidly before each beam delivery.

A fourth process embodiment can include taking the MRI data and performing reoptimization of the IMRT treatment plan on a moment-by-moment basis during the delivery of each part of each radiation beam in a single radiation delivery to improve the accuracy of the treatment delivery. This process can also include that the first process be performed in real-time simultaneously with the radiation delivery. The process can include the use of parallel computation that employs one or more computers beneficially connected via a low latency local network or a secure connection on a wide area network to greatly enhance the speed of the algorithms known in the art for MRI image reconstruction, deformable image registration, dose computation, and IMRT optimization.

According to alternative embodiments, a surgical guidance device and a process are provided for performing temporal- and spatial-resolution MRI of the anatomy and disease of a patient during various types of surgical procedures. Descriptions above of imaging systems for radiation treatment systems are also applicable to the following embodiments that involve surgical guidance systems. In a beneficial embodiment, a surgical guidance system comprises an open MRI that allows for access to the patient for performance of a surgical procedure, be it performed by a surgeon or by an automated device, such as a surgical robotic device.

Figure 13:
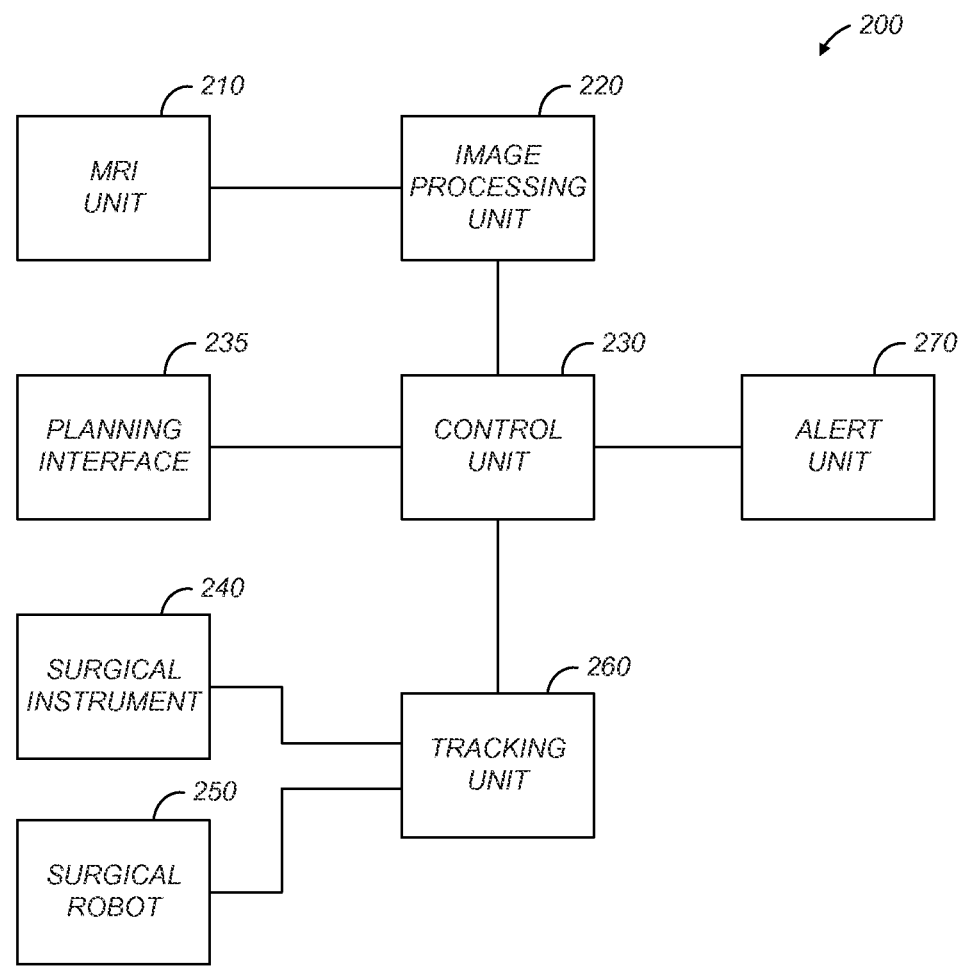
FIG. 13 shows a block diagram of a surgical guidance system according to the present disclosure.

Referring to FIG. 13, an embodiment of a surgical guidance system 200 includes an MRI unit 210, or an alternative imaging source, that preferably allows for noninvasive and non-ionizing radiation-based imaging of a patient's internal anatomy. FIG. 13 also shows an image processing unit 220, which can optionally be used to receive data generated by the MRI unit 210 and provide real-time image processing for converting the data into images that can be used for monitoring patient anatomy. The information produced by the image processing unit 220 can be provided to a control unit 230. Alternatively, data taken directly from the MRI unit 210, which may be referred to herein as "image data," may be interpreted or analyzed directly using methods known in the art to detect motions or changes in anatomy before or without passing the data to the image processing unit 220. The control unit 230 can receive information about a planned or ongoing surgical procedure from the surgeon or other personnel via a planning interface 235. The control unit 230 can optionally also receive information about an ongoing surgical procedure by receiving information about a trackable surgical instrument 240 and/or an automated surgical robotic device 250 via a tracking unit 260. Additionally, or alternatively, the control unit 230 can infer information about an ongoing surgical procedure based on imagery provided from the image processing unit 220. The control unit 230 can provide information to personnel monitoring the surgical procedure via an alert unit 270. Information provided via the alert unit 270 can include information indicative of one or more pre-defined conditions, and the information can be provided in one or more of a variety of different forms including, but not limited to, visual information and/or audible information. The visual information can include, for example, images and/or textual information. The audible information can include, for example, synthesized voice, voice recordings, and/or alarms.

The units depicted in FIG. 13 and described herein are for purposes of illustrating various functions, and as such the various units are not necessarily representative of separate elements. For example, a computer or other processor-based system can be used for performing the operations described herein of one or more of the image processing unit 220, the control unit 230, the planning interface 235, the tracking unit 260, and/or the alert unit 270. Also, one or more of the image processing unit 220, the control unit 230, the planning interface 235, the tracking unit 260, and/or the alert unit 270 can be integrally combined as a single device and/or can be integrally combined with the MRI unit 210.

The present disclosure thus includes a surgical guidance system for monitoring and/or guiding surgical interventions using noninvasive and non-ionizing radiation-based imaging by an MRI unit 210 or the like. The MRI unit 210 provides rapid volumetric imaging. The resulting images can be processed using deformable image registration in order to provide for real-time volumetric imaging, for example so that one can see a heart beat, lungs expand and contract, organ movement, arteries, formation of blood pools, etc. The real-time imaging can then be monitored by computerized control unit 230, which can continually analyze the imaging data in real time, determine if there are risks or deviations from the surgical plan, and if so, issue appropriate warnings or alerts to the surgeon and/or other personnel via the alert unit 270.

Figure 14:
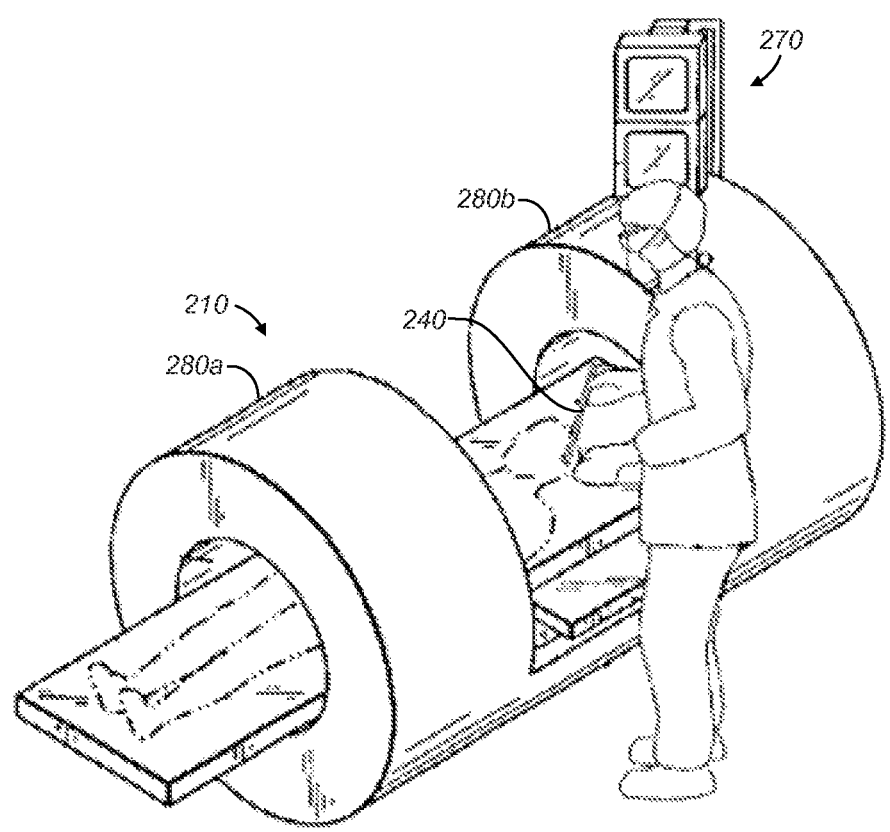
FIG. 14 shows a perspective view of an embodiment of the surgical guidance system shown in FIG. 13.

As shown in FIG. 14, the MRI unit 210 can include a split main magnet, where each have of the main magnet is housed in a respective one of the first and second main magnet housings 280a and 280b. The MRI unit 210 can also include split gradient coils, split RF shield, split T/R coil, and/or T/R surface coils (not shown). For example, the MRI unit 210 can include coils and/or shielding as disclosed in copending U.S. patent application Ser. No. 12/951,976, filed Nov. 22, 2010, titled "SELF-SHIELDED GRADIENT COIL," which is hereby incorporated herein by reference.

The split-magnet MRI unit 210 can image the anatomy of a patient, particularly the portions of the patient's anatomy that are positioned in the gap between the first and second main magnet housings 280a and 280b. The split-magnet MRI unit 210 also allows unobstructed access to the region of the patient being imaged (inside the imaging field of view) simultaneously to the performance of the surgical procedure. This allows the MRI unit 210 to continuously image the patient as surgery is being performed, where the images are of the region of the patient where the surgery is being performed. This also allows the surgical guidance system 200 to image a patient during surgery, as the surgical procedure is being performed, without repositioning the patient and/or imaging equipment.

A non-limiting example of a use of the surgical guidance system 200 can involve the use of the surgical guidance system 200 in connection with a surgical procedure. The process can begin with the surgical procedure being planned and images being acquired on as many high-resolution imaging devices as can be useful to the procedure (e.g., PET-CT, SPECT, 3 or 7 T MRI, etc.), as well as on the system 200 just before the surgical procedure commences. These image sets can be fused via a deformable image registration algorithm to form a primary planning image set.

The planning interface 235 provides a means for the surgeon, clinician, or other personnel to prepare a surgical plan. The planning interface 235 can include, for example, a computer or other processor-based system. In some embodiments, the planning interface 235 can include known surgical planning software and/or surgical planning capabilities. The planning interface 235 can include a keyboard, touch-screen, cursor-control device (e.g., trackball or mouse), or other such means for allowing a user to prepare a surgical plan. The planning interface 235 can then provide the surgical guidance system 200 with surgical parameters based on the surgical plan. The surgical plan thus will preferably include parameters that should be monitored by the system 200 during the surgical procedure. The parameters can vary depending on several factors, and can include threshold values that, if satisfied, can cause the system 200 to issue an alert via the alert unit 270.

For example, using the planning interface 235, the surgeon can define segmented anatomy for protection, resection, anastomosis, etc. The MRI unit 210 and image processing unit 220 can produce high-quality planning scans that are displayed by the planning interface 235. A clinician can interact with the planning scans using the planning interface 235 to create a plan for segmenting anatomy, set targets for excision, plan an anastomosis procedure, or any of many other known surgical procedures. Also, the planning interface 235 can be used to define surgical pathways as regions that represent routes that the surgeon intends to follow for entering the patient's body with surgical instruments. The planning interface 235 can be used to mark organs as targets of the surgical procedure (e.g., a tumor may be marked for excision). The planning interface 235 can be used to mark margins around organs for the surgical procedure (e.g., margins may be marked around a tumor for excision). The planning interface 235 can be used to define the extent of allowable puncture or penetration into an organ. The planning interface 235 can be used to mark organs or regions for preservation from invasion by surgical instruments (e.g., regions containing major nerves or arteries can be marked for preservation). The planning interface 235 can be used to define the volume of tissue to be resected, including margins if required. Any of these and other surgical planning parameters can be defined using the planning interface 235 and electronically stored as a surgical plan for the surgical procedure. It will be appreciated that these parameters include alert threshold values that can be expressly indicated by a surgeon, clinician, or other personnel using the planning interface 235, and/or can include alert threshold values that are inferred by the planning interface 235 based on planning information that is input into the planning interface 235 by a surgeon, clinician, or other personnel.

For example, a surgical plan can be created for a surgery to resect a tumor, which may include removal of a portion of a kidney. Pre-surgical images of the region surrounding the tumor can be provided to the planning interface 235. The surgeon can interact with the planning interface 235 to identify the portion of the kidney to be removed, for example by circling, marking, or otherwise identifying the portion to be removed. The surgeon may also observe a potentially hazardous region, such as a nearby artery that should be avoided. The surgeon can then also identify the artery, again by circling, marking, or otherwise identifying the artery using the planning interface 235. The surgeon can also use the planning interface 235 to identify other nearby organs, for example the liver and bowel, that the surgeon does not want to damage. All of this information can then become part of the surgical plan that will be monitored by the surgical guidance system 200 during the surgery. In this example, the surgical guidance system 200 would monitor the surgery in real time and issue alerts if the surgeon nears the artery or the bowel, or if the surgeon is at or near the limit of the amount of kidney to be removed. The surgical guidance system 200 can also watch for other conditions, such as pooling blood, irregular heart beating, or irregular breathing. Also, since the surgical guidance system 200 can track the movement of tissue using volumetric, deformable image registration imaging in real time during surgery, the control unit 230 can track movement of the tissue associated with the tumor as the surgeon is operating in order to allow the surgeon to stay on the surgical path and ensure that all of the tumor is safely removed.

Thus, the surgical guidance system 200 can allow a surgeon to input a plan for a surgery, and then track the surgery in real time and alert the surgeon as to their progress, for example if they are about to or have just violated some requirement or safety constraint. In order to accomplish this, the parameters that are defined using the planning interface 235 can be monitored by the control unit 230. Also, or alternatively, the control unit 230 can monitor predefined or default parameters that may not necessarily be specified via the planning interface 235. For example, the control unit 230 can be configured to monitor surgical procedures for undesirable conditions, such as excessively large motions, pooling of blood, and/or lack of blood flow. The control unit 230 can track organ motion and identify such conditions as blockages or blood pooling based on changes in data received from the MRI or images received from the image processing unit 220 through, for example, using known algorithms for detecting and/or tracking variations in image intensity and/or data representative of patient anatomy.

During the surgical procedure, the control unit 230 can continuously receive data representative of real-time images of patient anatomy generated by the MRI unit 210 and, optionally, image processing unit 220. The control unit 230 can monitor the parameters of the surgical plan using the received image data and deformable image registration during the surgical procedure to aid the surgeon in performing a safe and successful surgical procedure by alerting the surgeon or other personnel in the event that one or more alert threshold values has been met or exceeded (e.g., a surgical tool is at or near a defined margin).

Thus, the surgical guidance system 200 allows for real-time MRI-based guidance during surgical procedures. The surgical guidance system 200 has the ability to perform fast volumetric and/or planar imaging during surgical procedures. Imaging may be performed by the image processing unit 220 at a spatial and temporal resolution that allows for the tracking of the movement and deformation of the patient's tissue during the surgical procedure. In some embodiments, the MRI unit 210 can generate MRI data, for example k-space data, and the image processing unit 220 can rapidly generate image data representative of images that have been reconstructed based on the MRI data generated by the MRI unit 210. In some embodiments, the image processing unit 220 can include, for example, a computer or other processor-based system. Also, in some embodiments, the image processing unit 220 can include an imaging system and/or operate according to image reconstruction methods as disclosed in U.S. Patent Application Publication No. 2010/0322497, filed Jun. 17, 2010, titled "SYSTEM AND METHOD FOR PERFORMING TOMOGRAPHIC IMAGE ACQUISITION AND RECONSTRUCTION," which is hereby incorporated by reference. Volumetric imaging can thus be employed over the surgical region of the patient's body at a resolution that allows for determining the spatial location of the anatomy with the resolution required by the surgeon. The temporal refresh rate for imaging is preferably acquired at the rate of human reflex and response, i.e., between ½ and ⅕ of a second. The rate can be lowered or raised to capture slower or faster physiological processes occurring in the patient. The imaging for anatomy tracking and monitoring can be of a lower signal to noise and spatial resolution than diagnostic imaging, and deformable image registration can be employed to correlate higher resolution, signal to noise and contrast imaging to the real-time tracking images. Thus, in some embodiments, the quality of the pre-surgical images produced by the MRI unit 210 for creating the surgical plan can be of a higher quality than the images produced by the MRI unit 210 during the surgical procedure for real-time tracking.

The segmented anatomy and regions can optionally be continuously tracked and auto-contoured by the image processing unit 220 using deformable image registration on the stream of real time image data based on MRI data generated by the MRI unit 210. Anatomy that is defined to be critical for sparing of damage, incision, or excision, can be monitored with low latency, e.g., less than a second, to warn the surgeon via the alert unit 270 with audible and/or visual signals of the risk of damaging the critical structure. Criteria for a safe procedure can be rapidly computed and, if a violation is detected or is extrapolated to be imminent, audio and visual warnings can be provided to the surgeon or other personnel. If requested or required, planar images and metrics can be displayed to show the surgeon or other personnel what issues are causing the alarm. In some embodiments, the alert unit can include display means for continuously displaying images based on image data generated by the MRI unit 210 and image processing unit 220, thereby allowing the surgeon or other personnel to monitor the progress of the surgical procedure. The control system 230 and/or alert unit 270 can be configured such that characteristics of alerts can change based on the type and/or severity of the conditions that triggered the alert. For example, sounds, symbols, colors, or other indicators issued by the alert unit 270 can vary such that the degree of a warning issued by the alert unit can be increased with increases in the extent of damage, penetration, or excision of an organ in question.

As illustrated in FIG. 13, the surgical guidance system 200 can include a tracking unit 260 configured for tracking one or more surgical instruments 240. Referring to FIG. 14, it should be appreciated that a large magnetic field is present at the location where the surgical procedure is taking place due to the ongoing MRI imaging that is occurring during the surgical procedure. Thus, any surgical instrument 240 used during a surgical procedure should be formed of materials that are very weakly, or not significantly, affected by being placed in the presence of an externally applied magnetic field, e.g., paramagnetic materials. However, in some embodiments, the surgical instruments 240 can include markers, or otherwise be visible to the MRI unit 210. The position of a surgical instrument 240 can then be distinguished and tracked by the control unit 230 based optionally on the appearance of the surgical instrument 240 in images generated by the image processing unit 220. Alternatively, the position of the surgical instrument 240 can be inferred based on such things as organ motion and/or deformation, and/or other changes to the appearance of anatomical structures that appear in the images generated by the MRI unit 210 where such changes are indicative of surgical intervention. In some embodiments, in addition to continuous monitoring of a surgical instrument 240, the control system 230 can detect deviations from a surgical path that was previously defined using the planning interface 235, and compute a new trajectory, which can then be visually and/or audibly relayed to the surgeon.

It will thus be appreciated based on the present disclosure that the disclosed devices and methods have the ability to account for deformations and motions of the patient's anatomy during surgery through real-time imaging. This ability is advantageous, since most organs in the human body inherently and naturally experience motions continuously. The surgical instrument itself can also cause deformations and displacements of organs during the procedure as it punctures, cuts, or presses against the patient's tissues. The disclosed devices and methods also have the ability to provide warnings to a surgeon, without necessarily requiring the surgeon to regularly watch a monitor displaying images. In addition, pointing devices are not required to find the "correct" plane or projection in which to view a procedure.

Figure 15:
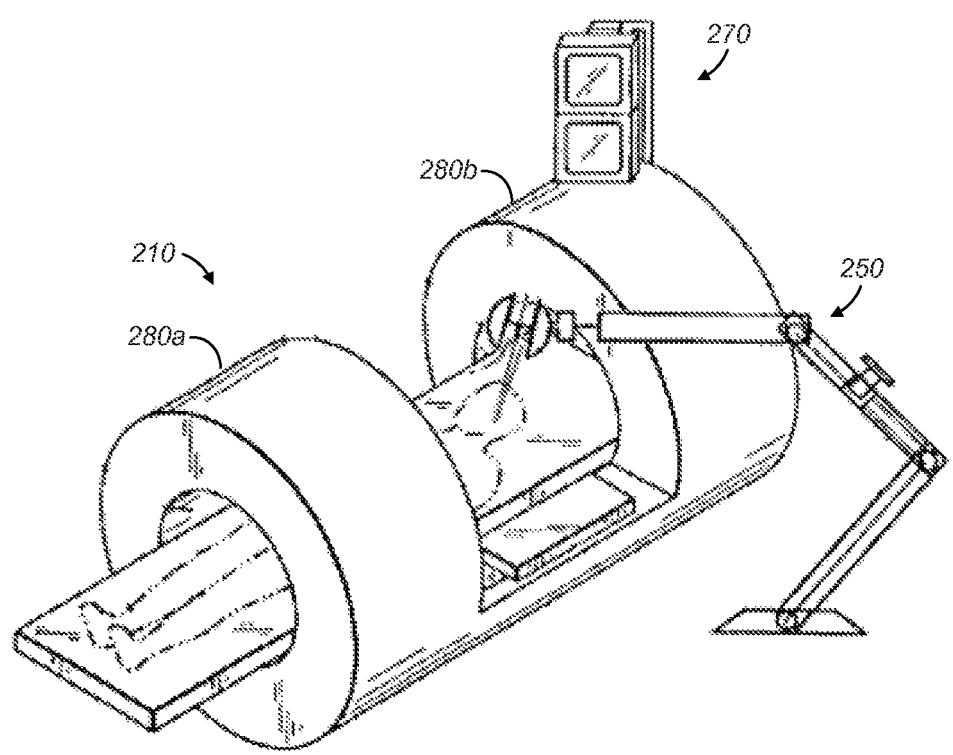
FIG. 15 shows a perspective view of an alternative embodiment of the surgical guidance system shown in FIG. 13.

As shown in FIG. 15, an automated surgical robotic device 250 can also be employed for performing a surgical procedure with, or in place of, a surgeon. For example, surgical robotic devices are known that can be used for performing a surgical procedure, including robotic devices having varying degrees of automation. The surgical guidance system 200 can provide feedback as described above to an operator and/or to the robotic device 250 during a surgical procedure. As discussed above, the feedback can include alerts based on a surgical plan input via the planning interface 235. The feedback can also include data used to control a surgical path of the robotic device 250. It will be appreciated that the surgical robotic device 250 can be any type of medical robot, and should preferably be capable of operating within a magnetic resonance imaging (MRI) scanner for the purpose of performing or assisting in image-guided interventions.

Although the illustrative embodiments of the present disclosure have been described herein with reference to the accompanying drawings and examples, it is to be understood that the disclosure is not limited to those precise embodiments, and various other changes and modifications may be affected therein by one skilled in the art without departing from the scope or spirit of the disclosure. All such changes and modifications are intended to be included within the scope of the disclosure as defined by the appended claims.

What is claimed is:

1. A surgical guidance system, comprising:
a magnetic resonance imaging (MRI) system configured for generating MRI data representative of a portion of a patient;
a planning interface for generating a surgical plan based at least in part on pre-surgical images and input information regarding surgical parameters for a surgical procedure, the surgical parameters including one or more position based parameters and one or more non-position based parameters;
a control unit for receiving image data based on the MRI data acquired during the surgical procedure and for monitoring the image data for conditions included in the surgical parameters of the surgical plan; and
an alert unit for issuing an alert based on instructions from the control unit,
wherein the control unit is configured to instruct the alert unit to issue the alert based on detecting at least one of the conditions included in the surgical parameters of the surgical plan.

2. The surgical guidance system of claim 1, wherein the MRI includes first and second main magnets separated by a gap.

3. The surgical guidance system of claim 1, wherein the MRI is configured such that images are captured substantially simultaneously with performance of the surgical procedure.

4. The surgical guidance system of claim 3, wherein the control unit is configured to employ the image data for monitoring a patient's response to the surgical procedure substantially simultaneously with performance of the surgical procedure.

5. The surgical guidance system of claim 4, wherein the monitoring of the patient's response to the surgical procedure includes monitoring changes to a patient's anatomy substantially simultaneously with performance of the surgical procedure.

6. The surgical guidance system of claim 5, wherein the control unit is configured to instruct the alert unit to issue the alert during the surgical procedure based on detecting at least one condition associated with the changes to the patient's anatomy.

7. The surgical guidance system of claim 1, further comprising a tracking unit for tracking a surgical instrument used for performing the surgical procedure.

8. The surgical guidance system of claim 1, further comprising a tracking unit for tracking a surgical robotic device performing the surgical procedure.

9. The surgical guidance system of claim 1, wherein the alert unit is configured to issue the alert in the form of at least one of visual information and audible information.

10. The surgical guidance system of claim 1, further comprising an image processing unit for receiving the MRI data from the MRI system and generating the image data based on the MRI data.

11. The surgical guidance system of claim 10, wherein the MRI system is configured for:
obtaining MRI data representative of a first quality of images before the start of the surgical procedure; and
obtaining MRI data representative of a second quality of images during substantially simultaneous performance of the surgical procedure, the second quality being lower than the first quality.

12. The surgical guidance system of claim 11, wherein the image processing unit is configured for generating image data representative of volumetric images from MRI data generated during the obtaining of MRI data representative of the second quality of images, and
wherein the generating of the image data representative of volumetric images includes using deformable image registration.

13. The surgical guidance system of claim 10, wherein the image processing unit is configured for generating image data representative of volumetric images based on the MRI data received from the MRI system.

14. The surgical guidance system of claim 13, wherein the image processing unit is configured for generating the image data representative of volumetric images using deformable image registration.

15. The surgical guidance system of claim 1, wherein the one or more non-position based parameters include an extent of allowable penetration into an organ, an allowable volume of tissue to be resected, an allowable amount of organ motion, and an allowable amount of blood pooling.

16. A surgical guidance system, comprising:
a magnetic resonance imaging (MRI) system configured for generating MRI data representative of a portion of a patient substantially simultaneously with performance of a surgical procedure on the patient;
a control unit for receiving image data representative of volumetric images based on the MRI data acquired during the surgical procedure and for monitoring the image data for predetermined conditions, the predetermined conditions associated with one or more position based parameters and one or more non-position based parameters; and an alert unit for issuing an alert based on instructions from the control unit, wherein the control unit is configured to instruct the alert unit to issue the alert based on detecting at least one of the predetermined conditions.

17. The surgical guidance system of claim 16, further comprising a planning interface for receiving at least one of the predetermined conditions.

18. The surgical guidance system of claim 16, wherein the MRI is configured such that MRI data is captured substantially simultaneously with performance of the surgical procedure.

19. The surgical guidance system of claim 18, wherein the control unit is configured to employ the image data for monitoring a patient's response to the surgical procedure substantially simultaneously with performance of the surgical procedure.

20. The surgical guidance system of claim 19, wherein the monitoring of the patient's response to the surgical procedure includes monitoring changes to a patient's anatomy substantially simultaneously with performance of the surgical procedure.

21. The surgical guidance system of claim 20, wherein the control unit is configured to instruct the alert unit to issue the alert during the surgical procedure based on detecting at least one condition associated with the changes to the patient's anatomy.

22. The surgical guidance system of claim 16, further comprising an image processing unit for receiving the MRI data from the MRI system and generating the image data representative of the volumetric images based on the MRI data.

23. The surgical guidance system of claim 22, wherein the MRI system is configured for:

obtaining MRI data representative of a first quality of images before the start of the surgical procedure; and obtaining MRI data representative of a second quality of images during substantially simultaneous performance of the surgical procedure, the second quality being lower than the first quality.

24. The surgical guidance system of claim 23, wherein the image processing unit is configured for generating the image data representative of volumetric images from MRI data generated during the obtaining of MRI data representative of the second quality of images, and wherein the generating of the image data representative of volumetric images includes using deformable image registration.

25. A surgical guidance method, comprising:

generating MRI data representative of a portion of a patient;

generating image data based on the MRI data;

generating a surgical plan based at least in part on pre-surgical images and input information regarding surgical parameters for a surgical procedure, the surgical parameters including one or more position based parameters and one or more non-position based parameters;

monitoring the image data for conditions included in the surgical parameters of the surgical plan; and issuing an alert based on detecting at least one of the conditions included in the surgical parameters of the surgical plan.

26. The surgical guidance method of claim 25, wherein the image data is representative of volumetric images based on the MRI data.

27. The surgical guidance method of claim 26, wherein the MRI data is captured substantially simultaneously with performance of a surgical procedure.

28. The surgical guidance method of claim 27, wherein the image data is monitored for a patient's response to the surgical procedure substantially simultaneously with performance of the surgical procedure.

29. A computer program product comprising at least one non-transitory computer readable storage device storing computer instructions that, when executed on at least one processor, cause the at least one processor to perform operations comprising:

generating MRI data representative of a portion of a patient;

generating image data based on the MRI data;

generating a surgical plan based at least in part on pre-surgical images and input information regarding surgical parameters for a surgical procedure, the surgical parameters including one or more position based parameters and one or more non-position based parameters;

monitoring the image data for conditions included in the surgical parameters of the surgical plan; and issuing an alert based on detecting at least one of the conditions included in the surgical parameters of the surgical plan.

* * * * *